US008690568B2

(12) United States Patent
Chapoulaud et al.

(10) Patent No.: US 8,690,568 B2
(45) Date of Patent: Apr. 8, 2014

(54) CUSTOM ORTHODONTIC APPLIANCE FORMING METHOD AND APPARATUS

(75) Inventors: Eric Chapoulaud, Pasadena, CA (US); Craig A. Andreiko, Alta Loma, CA (US); Mark A. Payne, Whittier, CA (US)

(73) Assignee: Ormco Corporation, Orange, CA (US)

( * ) Notice: Subject to any disclaimer, the term of this patent is extended or adjusted under 35 U.S.C. 154(b) by 367 days.

(21) Appl. No.: 09/941,151

(22) Filed: Aug. 28, 2001

(65) Prior Publication Data

US 2002/0028417 A1    Mar. 7, 2002

Related U.S. Application Data

(63) Continuation of application No. PCT/US00/35558, filed on Dec. 29, 2000.

(60) Provisional application No. 60/173,890, filed on Dec. 29, 1999.

(51) Int. Cl.
*A61C 3/00* (2006.01)

(52) U.S. Cl.
USPC .......................................................... 433/24

(58) Field of Classification Search
USPC ................................ 433/2, 24, 29, 6; 705/2, 3
See application file for complete search history.

(56) References Cited

U.S. PATENT DOCUMENTS

| 5,131,844 | A | 7/1992 | Marinaccio et al. | |
| 5,431,562 | A | 7/1995 | Andreiko et al. | 433/24 |

(Continued)

FOREIGN PATENT DOCUMENTS

WO    WO98/58596    12/1998

OTHER PUBLICATIONS

K. Yamamoto et al., *Optical Measurement of Dental Cast Profile and Application to Analysis of Three-Dimensional Tooth Movement in Orthodontics*, Frontiers of Medical and Biological Engineering, vol. 1, No. 2, pp. 119-130 (1988).

(Continued)

*Primary Examiner* — Heidi M Eide
(74) *Attorney, Agent, or Firm* — Wood, Herron & Evans, LLP

(57) ABSTRACT

A system (10) and method by which an orthodontic appliance (25) is automatically designed and manufactured from digital lower jaw and tooth shape data of a patient provides for the scanning of the mouth of a patient (12), preferably from a model (20) of the patient's mouth, to produce a three-dimensional digitized model (26) of the shapes of the patient's teeth and their positions in the patient's mouth. Then a computer (30) calculates the post-treatment positions of the teeth and produces three-dimensional images of the teeth, individually and in their calculated positions. An interactive computer link between the doctor's office (11) and the appliance manufacturing facility (13) allows an orthodontist (14) to control the patient's archform and to modify the suggested computer-determined positions and orientations of the teeth in six degrees of freedom, and to experiment with new positions, extractions, over-corrections and other variations, with the computer recalculating the tooth positions with high precision for the approval of the orthodontist. The appliance is automatically designed according to the final design, which also can be interactively modified and approved by the orthodontist, with the computer recalculating the effects on the treatment as a result of the doctor's changes. Brackets (81) are fabricated as an integrated set, either by cutting slots therein or by building the brackets in layers by, for example, stereo lithography. Three-dimensional custom jigs (87) are automatically made to exactly position the brackets on a patient's teeth.

13 Claims, 23 Drawing Sheets

(56) References Cited

U.S. PATENT DOCUMENTS

| | | | |
|---|---|---|---|
| 5,975,893 A | 11/1999 | Chishti et al. | 433/6 |
| 6,205,716 B1 * | 3/2001 | Peltz | 52/36.2 |
| 6,217,334 B1 * | 4/2001 | Hultgren | 433/215 |
| 6,227,850 B1 | 5/2001 | Chishti et al. | 433/24 |
| 6,244,861 B1 | 6/2001 | Andreiko et al. | 433/3 |
| 6,471,512 B1 * | 10/2002 | Sachdeva et al. | 433/24 |
| 6,575,751 B1 * | 6/2003 | Lehmann et al. | 433/223 |
| 2001/0002310 A1 | 5/2001 | Chishti et al. | |

OTHER PUBLICATIONS

P. R. Crawford, *CAD/CAM in the Dental Office: Does it Work?*, Journal, vol. 57, No. 2, pp. 121-123, Feb. 1991.

* cited by examiner

CUSTOM ORTHODONTIC APPLIANCE FORMING METHOD AND APPARATUS

This application is a continuation of International Patent Application No. PCT/US00/35558, filed Dec. 29, 2000, which is an International Application of U.S. Provisional Patent Application Ser. No. 60/173,890, filed Dec. 29, 1999, both of which are hereby expressly incorporated herein by reference in their entirety.

This application is related to U.S. patent application Ser. No. 09/431,466, filed Nov. 1, 1999, which is a continuation of U.S. patent application Ser. No. 08/960,908, filed Oct. 30, 1997, now U.S. Pat. No. 6,015,289, which is a continuation of U.S. patent application Ser. No. 08/456,666, filed Jun. 2, 1995, now U.S. Pat. No. 5,683,243, which is a divisional of the following U.S. patent applications, each of which was filed on Nov. 9, 1992:

Ser. No. 07/973,973 entitled Method of Forming Custom Orthodontic Appliance, now U.S. Pat. No. 5,431,562, Ser. No. 07/973,965 entitled Custom Orthodontic Brackets and Bracket forming Method and Apparatus, now U.S. Pat. No. 5,454,717, Ser. No. 07/973,947 entitled Custom Orthodontic Archwire forming Method and Apparatus, now U.S. Pat. No. 5,447,432, Ser. No. 07/973,844 entitled Method and Apparatus for Forming Jigs for Custom Placement of Orthodontic Appliances on Teeth and Jigs Formed Therewith, now U.S. Pat. No. 5,368,478; and is also related to U.S. Pat. Nos. Re 35,169; 5,139,419; 5,395,238 and 5,518,397.

All of the above related patents and applications are assigned to the assignee of the present application, and all are hereby expressly incorporated by reference herein.

FIELD OF INVENTION

The present invention relates to the design, manufacture and use of orthodontic appliances for the straightening of teeth, and more particularly, to the automated design, manufacture and use of custom orthodontic appliances based on individual patient anatomy and to the treatment of patients therewith.

BACKGROUND OF THE INVENTION

The orthodontic treatment of patients has as its fundamental objective the repositioning or realignment of the teeth of a patient in the patient's mouth to positions where they function optimally together and occupy relative locations and orientations that define opposed and cooperating smooth archforms. A common technique for achieving this objective is to position orthodontic brackets on a patient's teeth such that archwire slots in the brackets will align when the teeth are in their corrected positions, and to place an elastic archwire in the slots that urges the teeth toward their corrected positions as the wire tends to straighten. In an ideal situation, a perfectly positioned, perfectly designed appliance used in this manner will theoretically move the teeth to their intended corrected positions without intervention in the form of "wire bending" by the orthodontist. With most appliances made to apply to standard statistically average dental anatomy, the ideal is seldom, if ever, realized.

The patents identified above describe the design, manufacture and use of custom orthodontic appliances designed and built with the aid of a computer. With such automated appliance design and manufacturing systems, the collection of data of the shapes of the patient's dental anatomy, the processing of the collected data to create an appliance in accordance with the treatment prescribed by an orthodontist, the precise and economic manufacture of the custom orthodontic appliance, and the efficient and accurate placement of the appliance on a patient's teeth are important.

Accordingly, there is a great need in orthodontics for a practical, reliable and efficient custom appliance automated design and manufacturing system, and method of providing custom appliances and treating patients therewith.

SUMMARY OF THE INVENTION

A primary objective of the present invention is to provide a practical, reliable and efficient custom appliance designing and manufacturing system and to provide a method of designing custom orthodontic appliances and treating patients therewith. A more particular objective of the invention is to provide for improved automation in orthodontic appliance design and manufacture, especially for custom orthodontic appliances.

A further objective of the present invention is to provide custom orthodontic appliance design and manufacturing involving an efficient and effective distribution of functions and decision making among the orthodontist, the appliance manufacturer and the specially programmed computer. Another objective of the present invention is to apportion tasks involved in the design and manufacture of custom appliances most efficiently between orthodontist and appliance manufacturing facility in accordance with the scale and other particulars of the individual practitioner operation, giving the orthodontist optimum control over the final archform and of the treatment process, while increasing the accuracy of treatment and the efficiency of use of the orthodontist's time and eliminating guesswork and sources of error.

Another objective of the present invention is to improve the practice of orthodontics by aiding the practitioner in achieving optimal treatment of patients and in more accurately determining and precisely achieving the placement of a patient's teeth, and particularly in enabling the performance of an orthodontic appliance and the results of orthodontic treatment to more closely conform to the appliance design and treatment plan.

An additional objective of the present invention is to provide more complete three-dimensional control in the design, manufacture and use of an orthodontic appliance and in the movement of the patients teeth in orthodontic treatment.

According to principles of the present invention, a system and method for designing and making a custom orthodontic appliance are provided. In the system and method, an orthodontist provides a record of three-dimensional dental anatomical information from the patient's mouth at the orthodontist's office or clinic and transmits the record to an appliance design facility or lab. From the digital model, a custom orthodontic appliance is designed by the lab on a computer in accordance with preprogrammed criteria and a prescription from the orthodontist. A custom orthodontic appliance is made from the computer generated design.

The record may be in the form of a physical model, usually in the form of a cast replica of the patients upper and lower jaws, with the teeth in their pretreatment positions, made from an impression or mold of the patient's mouth made by the orthodontist. Where the physical model is transmitted to the lab, the lab scans the model with a laser or other optical scanner, or other type of scanner, preferably a non-contact scanner. The scanning produces a three-dimensional digital model of the patients mouth, including the shapes of the teeth and jaw of the patient and the positions of the teeth in the patient's mouth. Alternatively, the scanning of the model can be carried out by the orthodontist at the orthodontist's office or digital information can be derived from a full oral scan directly of the patient's mouth, and the digital scanned information then transmitted to a lab remote from the office.

The scanning is preferably carried out with a laser scanner, first in a low resolution mode which locates the model on a workpiece support and provides a basis for identifying the portion of the scanned image that is of interest and identifying the various teeth, boundaries and other anatomical features to be digitized. Then, in high resolution mode, the features that were identified in the low resolution mode are scanned to produce high resolution, three-dimensional image files of the shapes of each of the teeth. An operator at the lab supervises the identification of landmarks and other properties and features of the scanned data. The landmarks include all of the cusps and incisal tips of the teeth, the central grooves and marginal ridges of the teeth, and gingival points on the facial and lingual sides of the teeth, as well as other landmarks described below.

The determination of tooth finish or posttreatment positions is carried out interactively with the orthodontist by communication with a computer at the appliance design facility. The computer first calculates a suggested posttreatment setup of the teeth, which the orthodontist can modify and have recalculated until the final treatment positions of the teeth have been approved by the orthodontist. This allows the orthodontist to move any of the teeth in six degrees of freedom: by torque, tip or rotation angles, mesial-distally, labial-lingually or occlusal-gingivally. The orthodontist can thereby test archforms, for example with and without extractions and with or without over-correction, and to view the posttreatment results on a computer screen, with the teeth as three-dimensional solid objects.

After the final tooth positions are decided upon, then a custom appliance is designed by the computer in accordance with the approved tooth finish position or posttreatment setup of the teeth. As with the tooth setup, the design of the appliance is interactively adjusted, tested and approved by the orthodontist. Once the appliance design is approved, the appliance is made by computer controlled equipment in accordance with the design.

The high resolution, three-dimensional data of the shapes of the teeth are used in the calculations of tooth finish positions and in the design of a custom orthodontic appliance to move the teeth to the calculated finish positions and to fit the appliance to the surfaces of the patient's teeth. The data may be used to design the shapes of the bases of orthodontic brackets to precisely conform to the surfaces of the teeth at the points thereon at which the brackets are to be bonded. The three-dimensional data is particularly beneficial when used to design the shapes of jigs to precisely conform to the surfaces of the teeth to uniquely position an appliance on the teeth, such as locating brackets at calculated ideal positions on the teeth for bonding thereto. Such jigs include any structure having a negative image of a tooth surface that functions to locate on one or more teeth an orthodontic appliance or other structure that is added to assist in the orthodontic treatment of a patient's teeth. Such jigs are beneficial in positioning fully custom designed brackets and other appliances as well as in positioning semi-custom or standard brackets at their ideal positions on a patient's teeth, or in locating any other structure for bonding to a tooth or to otherwise position on patient's teeth.

The calculations of the finish positions of the teeth locate the crown long axes of the teeth in three dimensions with the torque, tip and rotation angles of the axes and planes containing the axes precisely determined as well as the x-y-z positions of the axes.

Manufacture of custom appliances includes the making of a generally arch-shaped appliance to move the teeth to their calculated finish or posttreatment positions on calculated archforms established in an interactive process between a computer and an orthodontist. The appliance type preferably is a straight wire orthodontic brace system that includes a set of orthodontic brackets bonded one to each of a plurality of a patient's teeth, usually a set of buccal tubes secured by bands or bonding to the most distal of the patient's teeth, and a set of archwires ligated in slots in the brackets. Retainers, positioners and other arcuate or generally arch-shaped appliances may be similarly designed by the system described herein, as well as other forms of orthodontic appliances.

The manufacture of archwires is accomplished by operating computer controlled equipment to shape one or more archwires of the custom designed appliance. Archwires may be so formed by feeding and bending wire from continuous wire stock, which is useful for wires of steel and similarly formable metals, using wire bending machinery controlled in accordance with a calculated archwire shape. Wires may also be formed by milling, cutting or otherwise imposing the calculated archwire curve on or in a plate or form, into which a wire is placed and annealed or otherwise heat treated, which is particularly useful for making archwires of high elasticity metals such as titanium or titanium containing alloys. Other types of orthodontic appliances or appliance accessories, such as brackets, retainers, positioners, or positioning jigs may be made by this process.

Orthodontic brackets of a set required to treat a patient may be formed by cutting slots in bracket bodies, each welded to a bracket base, all of which bases of the set are formed of a single sheet of metal bracket base material. The bases may be custom formed to curve to conform to the surfaces of the patient's teeth or may be curved to the standard curvatures of statistically average teeth. Whether the bases are custom or standard in curvature, slots may be cut into the brackets to the in-out depth, rotation, tip and torque that are custom to the ideal appliance for the patient. The single sheet of metal serves as a work-holder to hold all of the brackets of the set in predetermined positions during the slot cutting procedure.

Orthodontic brackets as well as other orthodontic appliances and appliance components may alternatively be formed by deposition of material in layers, shaped according to the cross sections of the appliance according to its calculated geometry. The materials so deposited can be made up of different materials that are differentially deposited to define the cross section shapes, may be one or more types of materials that are selectively activated, cured or hardened, such as by exposure to light, heat or chemicals, and with the selectivity being carried out in accordance with the calculated appliance shape data produced in the custom appliance designing process. In forming brackets using the layer deposition process, one or more intermediate objects may be formed from which an appliance having a surface shaped to matingly conform to the surface of the crown of a tooth may be formed. Such intermediate objects may be in the form of a mold or a pattern for the making of a mold.

For example, different waxes may be deposited, for example, by a jet printing process to build up the bracket shape as a stack of layers producing a three-dimensional wax pattern, which then can be used to form a mold to produce a custom bracket by an investment casting process. Materials out of which the brackets are to be ultimately made may also be deposited by a dot printing process, for example, depositing metal and binder mixtures that may be of different compositions to define the shape of the appliance being produced. Alternatively, homogeneous materials may be deposited but selectively cured, using laser energy or some other high resolution selective process. Such processes may produce a multi-layered object of material that will withstand heat or a solvent used to remove the material surrounding the portion of the material defining the appliance or appliance part, leaving an object that becomes the bracket, for example, or becomes a pattern for a mold to form the appliance or appliance part.

Jigs for the positioning of one or more brackets or other appliances or appliance parts are formed by any of several possible processes, for example, that produce a cavity shaped to precisely conform to the occlusal surface of the crown of the one of the patient's teeth on which one or more appliances are to be positioned for bonding. The appliance or appliances to be bonded are configured in cooperation with the jig to attach to the jig so that each appliance will be located at one and only one position on the surface of the tooth when the jig is fitted in its unique position and orientation on the occlusal surface of the tooth. Preferably, when a set of brackets and bracket positioning jigs is provided according to the system and method described herein, the brackets and jigs are pre-attached to each other in predetermined relative positions and orientations at the appliance manufacturing facility so that the jigs need be removed only after the orthodontist has bonded the brackets to the teeth of the patient for which the appliance is designed.

These and other objectives and advantages of the present invention will be more readily apparent from the following detailed description of the drawings in which:

DETAILED DESCRIPTION OF THE DRAWINGS

Figure 1:
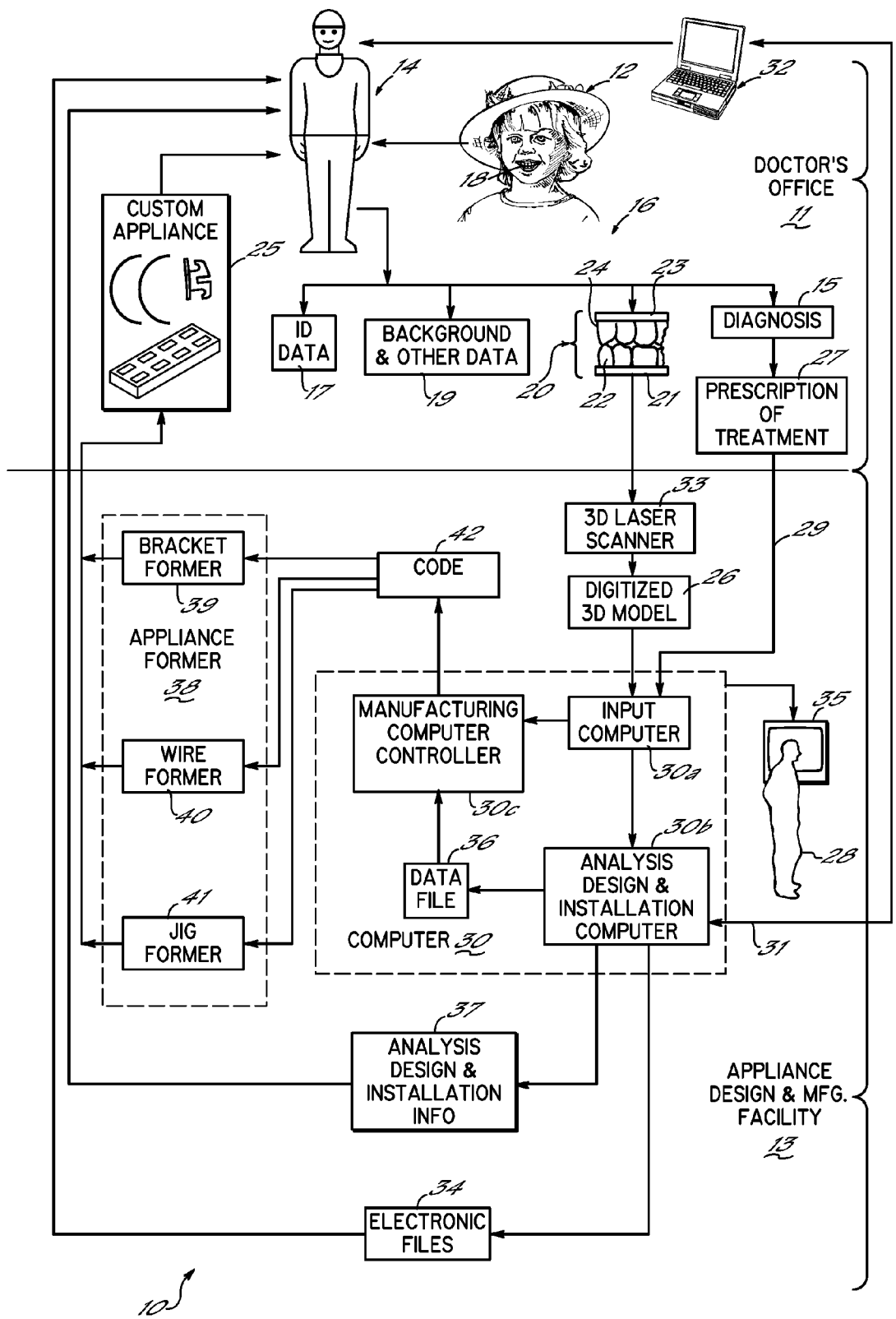
FIG. 1 is a block diagram illustrating one embodiment of a custom orthodontic appliance designing and manufacturing system according to one embodiment of the present invention.
Figure 2:
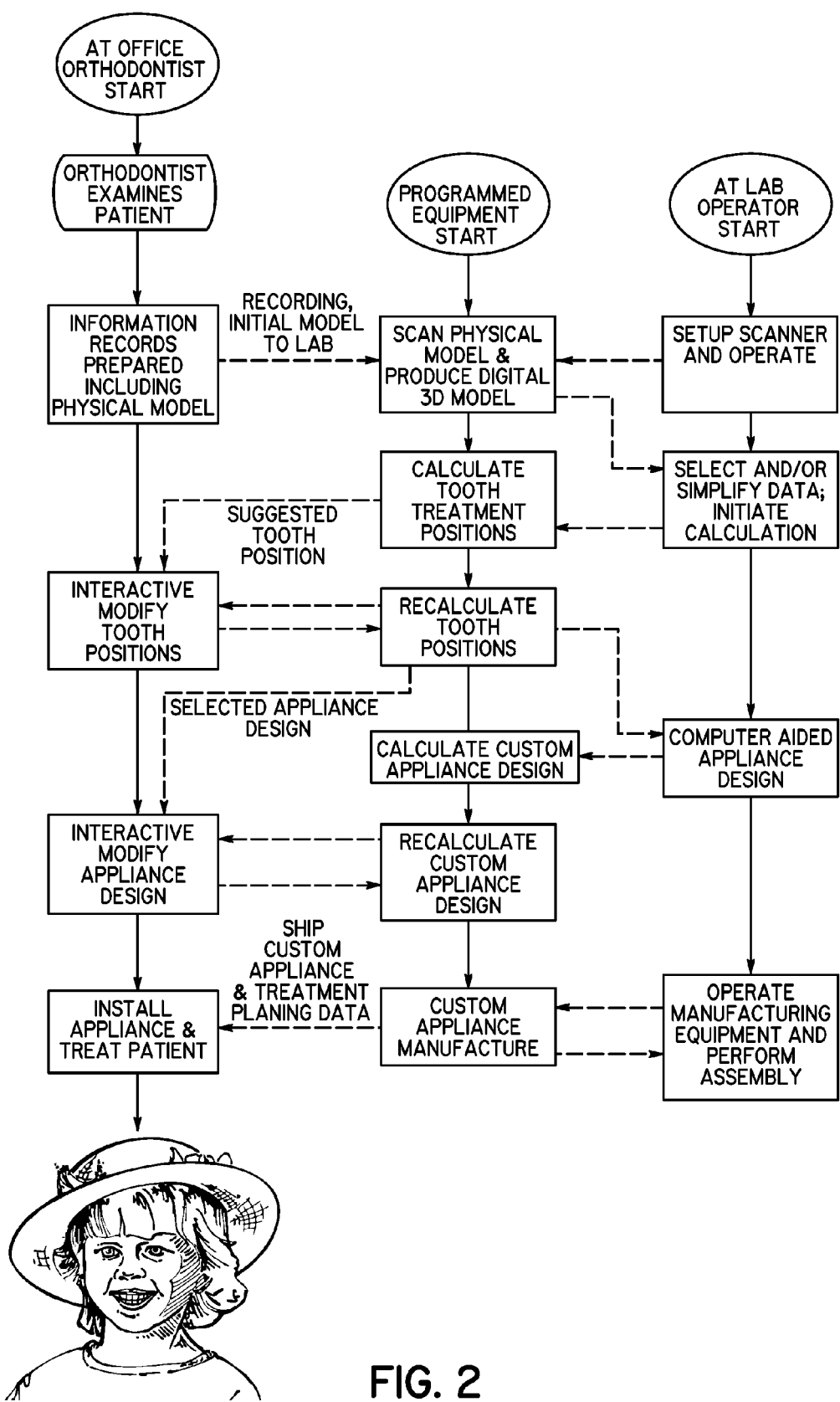
FIG. 2 is a flowchart of one embodiment of the process of the present invention performed with the system of FIG. 1.

One embodiment of a custom orthodontic appliance manufacturing system 10 according to principles of the present invention is diagrammatically illustrated in FIG. 1. A process by which the system 10 may operate is illustrated in the chart of FIG. 2. The system 10 may be distributed among a plurality of locations, preferably between two locations, which include an orthodontist's office 11 and an orthodontic appliance designing and manufacturing facility or lab 13. The actions and decision making in the operation of the system 10 is distributed among three paths, including (1) the orthodontist 14 located at the office 11, (2) data gathering and processing equipment 30,33 and appliance manufacturing equipment 38, located mostly at the lab 13 but some of which may be located at the office 11, and (3) the lab operator 28 located at the facility 13. These three paths are represented by the three columns in FIG. 2, wherein the steps performed by the orthodontist are illustrated at the left, the steps performed by the computers and other equipment are illustrated in the center, and the steps performed by operators at the facility 13 are illustrated at the right. The dashed lines represent interactions, including exchanges of information, between the paths.

At the office 11, orthodontic treatment of a patient 12 is undertaken by an orthodontist 14, at the office 11, who makes a diagnosis 15, which is reduced in form to one of several data records 16. The records 16 are generated as part of the case information necessary to determine the patient's condition, prescribe the appropriate treatment, and specify the type of orthodontic appliance to implement the treatment of the patient 12. The case information data records 16 include information identifying the patient 12, anatomical data of dental and related shapes from the mouth 18 of the patient 12, and preferably other background information 19, such as racial and genetic information that has a relation to the dental anatomical characteristics of the patient that can be useful in selecting or designing treatment and the types of appliances to be used in the treatment.

Examination of the patient 12 by the orthodontist 14 involves the traditional application of the skill, knowledge and expertise of the orthodontist 14, and results in the creation of a detailed anatomical record of the shape and initial maloccluded locations of the teeth in the patient's mouth as well as the jaw structure of the patient 12. This detailed anatomical record may be in the form of a physical three-dimensional model 20 of the patient's mouth 18. Such a model 20 is typically a cast formed in a mold impression, made by the orthodontist 14, of materials such as alginate for example, of the patient's mouth 18, according to traditional procedures known to orthodontists. The model 20 is usually made of plaster and includes a mandibular casting or model 21 of the patient's lower jaw or mandible 22 and a maxillary model 23 of the patient's upper jaw or maxilla 24, each replicating the shapes of the patient's teeth in their relative pretreatment positions in the respective lower and upper jaws.

The orthodontist 14 determines the general type of orthodontic appliance with which the patient 12 is to be treated, as well as certain parameters of such an appliance. In the system 10, the appliance is a custom orthodontic appliance 25 of a generally arcuate or arch-shaped shape that the orthodontist 14 installs on the patient's teeth. To initiate production of the appliance 25, the orthodontist 14 transmits the physical model 20 to the appliance designing and manufacturing facility 13 along with the other data records 16, including a prescription 27 wherein the orthodontist sets forth a treatment plan to be applied to the patient and specifies a result to be achieved by the treatment. As an alternative to transmitting a physical model 20 to the facility 13, a digital model 26 may be generated at the orthodontist's office 11, either directly from the patient's mouth 18 without the use of a physical model 20, or from the physical model 20, so that the digital model 26 may be transmitted to the appliance manufacturing facility 13.

The prescription 27 may include a specification of techniques that are to be included in the treatment and a designation of an orthodontic appliance to be employed. Historically, such a prescription 27 is not so detailed as to include precise mathematical arrangements or movements of the teeth that the treatment will produce, but may include treatment goals, including some expressed in numerical values representing the arrangement of the teeth that is sought.

The facility 13 is provided with one or more trained operators 28. An operator 28 supervises the input of data into the computer 30, including the data of the digitized model 26 and also data of treatment plan and appliance design decisions or parameters. This data may be input into the input computer 30a or another computer 30b specifically dedicated to the design of the custom appliance 25. An operator 28 may also add input to or control operation of appliance manufacturing equipment 38 controlled by computer 30, such as by computer 30b or by another computer or machine controller 30c to manufacture the appliance 25. Where the inputting, design and manufacture are performed at the appliance facility 13, the computers 30a, 30b and 30c may be the same computer 30 or separate computers or controllers that are linked to each other or otherwise exchange data.

Where the physical model 20 itself is transmitted to the facility 13, the operators 28 operating scanning equipment 33 to generate digital information 26 in the form of a three-dimensional digital model of the patient's teeth while in their pretreatment positions in the patient's mouth. Alternatively, the digital model 26 is received by the operator 28 from the orthodontist 14. The digital model 26 produced from the physical model 20 or received directly from the orthodontist 14 is input into a computer 30a. The input computer 30a is particularly useful to manage the generation of the digital information 26 by controlling the scanning of the physical model 20, for example, with a three-dimensional laser scanner 33, to produce the 3-D digital model 26. The input computer 30a utilizes interaction from the operator 28 to efficiently guide the scanner 33 in the scanning of areas on the surface of the teeth and in the selection of particularly useful orthodontic parameters from graphic images produced by the scanner 33 on a screen 35 of a display connected to the inputting computer 30. The scanner 33 acquires 3-D data from the three-dimensional surfaces of the physical model 20 and inputs the acquired data to the computer 30a, which produces the digitized anatomical information or digital model 26 in machine readable form for analysis by the appliance design computer 30b. The operator 28 inputs information used to simplify the 3-D data to define the teeth and other dental anatomy of the patient in terms of landmarks or other criteria that are useful in the setup of the case or the design of the occlusion that is the objective of the treatment plan. Algorithms may also be used to determine these landmarks and other criteria with little or no operator interaction.

The scanner 33 may include one or more video cameras, mechanical probes, laser or other optical scanners, ultrasonic scanners, moiré image scanners or other forms of imaging or measurement hardware that alone, or in combination with other such components, produce a three-dimensional digital model of the surface of the patient's teeth and mouth tissue defining the shape of the patient's jaw. While a laser scanner 33 is illustrated, other types of scanners, preferably non-contact scanners, may be used, and as technology progresses, many types of such scanners are becoming available, such as digital optical scanners that use coded pulsed white light.

The data of the 3-D digital model 26 is processed, along with other data from the orthodontist 14, and interactive selections made by the operator 28 and/or the orthodontist 14 to determine tooth finish or treatment positions of the patient's teeth. Preferably, the initial determinations of the final treatment positions of the teeth are made from the 3-D digital model, including particularly tooth shape and jaw shape data, from the prescription information 27 from the orthodontist 14, from the other information 16 from the orthodontist 14, and from selections made by the operator 28 which aids the computer 30b in interpreting and simplifying the data for processing. The tooth treatment position calculations made in the design computer 30b use programs containing algorithms such as those described in the related patents and applications identified above and others described below. The computer 30b may also utilize interactive methods by which an operator 28 monitors, selects options, and modifies the calculation of tooth finish positions as well as appliance design.

The initial determinations of finish position produce a precise prediction of the prescribed treatment, taking into account the programmed algorithms and the exact three-dimensional shapes of the tooth surfaces. This results in an ideal dental or clinical archform or other intermediate or final tooth arrangement in which a treatment digital model, in the form of three-dimensional computer images and numerical data, is provided for review, revision or approval by the orthodontist 14. Such a digital model may or may not be in the form of a mathematical archform model in which some equation or formula is used to articulate an arcuate, that is a generally arch-shaped arrangement of the teeth. A digital model of a dental archform may be in the form of digital data from which the teeth can be represented or displayed in their generally arch-shaped arrangement for human evaluation. Preferably, the data is in a form that is capable of computer analysis. An image of the proposed treatment result is communicated digitally to the orthodontist 14 through a computer network or other data link 31 connected between the design computer 30b at the appliance design facility 13 and an interactive computer terminal 32 at the office 11 of the orthodontist 14. The link 31 along with software in the computers 32 and 30b provide an interactive system through which the orthodontist can manipulate the initial determinations of calculated treatment positions as well as the course of treatment in response to which the design computer 30b recalculates the final treatment positions of the teeth and generates display data for further review, revision or approval by the orthodontist 14.

Once the tooth treatment positions are approved by the orthodontist 14, the computer 30b automatically designs the appliance under the supervision of an operator 28. As a digital appliance design is produced, the design information, which includes three-dimensional design display and numerical design data, is provided over the link 31 to the terminal 32 for interactive adjustment and ultimately approval by the orthodontist 14.

When the appliance design has been approved by the orthodontist 18, the analysis and design computer 30b produces archive files 34 that are written with all of the relevant information of the analysis and the history and prescribed treatment of the patient 14. Calculated information for the patient is stored in a patient data file 36. From the calculations, the manufacturing computer 30c produces machine readable code 42 for operating digitally controlled manufacturing equipment 38 to produce the appliance 25. An instruction document or file 37 may also be produced, either by the computer 30b or the computer 30c, of information to aid the orthodontist 14 in treating the patient 14 with the custom appliance 25.

For manufacture of custom orthodontic appliances of the types most commonly used at the present time, the manufacturing equipment 38 preferably includes an appliance bracket forming machine 39 which produces custom brackets for the appliance 25. Automated bracket making can be carried out by casting or molding of the brackets from molds made by the automated machines, by cutting slots at calculated angles or machining other features in preformed blanks, or by other automated bracket making methods. The machine 39 may shape the surfaces of preformed bracket bases, providing a design option of torquing the teeth by either the bracket slot or base, as may be best for various bracket materials. The equipment 38 may also include an appliance archwire bending machine or other type of wire forming machine 40 to produce custom shaped archwires for the appliance 25. The equipment 38 in most preferred embodiments includes a machine for forming components to aid in the installation of the appliance 25 by insuring that the appliance is located on the surfaces of the teeth when installed. In archwire and bracket type appliances, this includes a machine 41 for the making of bracket placement jigs, which cuts or otherwise forms three-dimensional tooth fitting recesses that prevent placement of the appliance on a tooth in all but the correct location on the tooth.

While conventional bracket and archwire appliances are illustrated and described, concepts described herein can be applied to other forms of orthodontic appliances. Where in the conventional appliance, individual brackets make connections between the appliance and the patient's teeth while archwires interconnect the teeth via the brackets to exert the treating forces among the teeth, a single piece appliance in which a resilient arch shaped element both interfaces with the teeth and exerts forces among the teeth can be used according to certain aspects of the invention. Similarly, the three-dimensional surfaces that may be provided on placement jigs to locate the appliance on the patient's teeth may be located on parts of an appliance itself, such as on the bracket itself or on a single piece generally arch-shaped appliance, so that the appliance is self-positioning or self-locating. Such a jig may or may not remain attached to the appliance or may or may not remain on the patient's teeth so as to facilitate initial or continued positioning of the appliance on the teeth.

Figure 3:
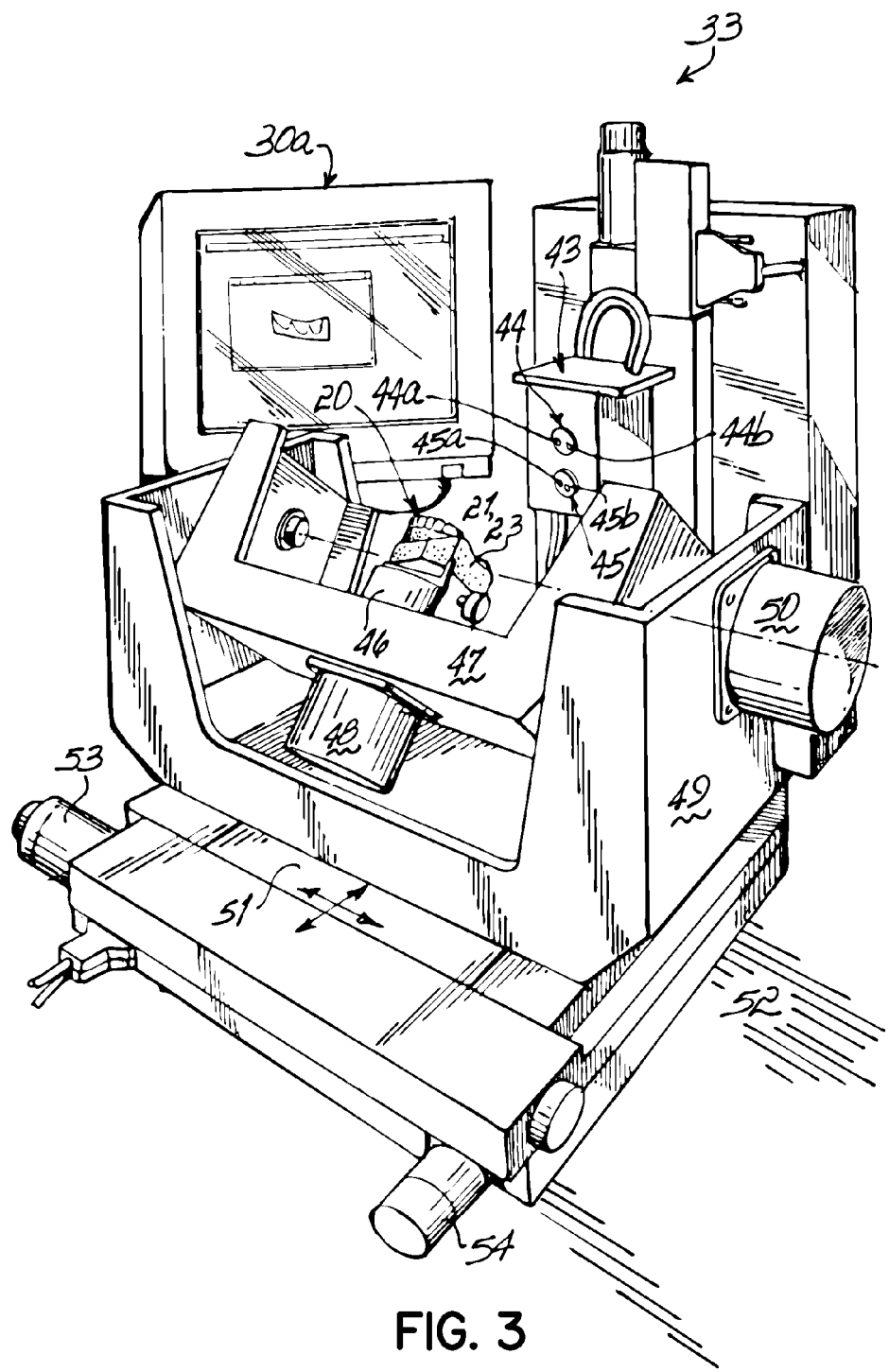
FIG. 3 is a perspective diagram of a three-dimensional graphics imaging scanner of the system of FIG. 1.

A suitable 3-D scanner 33 is illustrated in FIG. 3 and includes a laser scanner assembly 43. The laser scanner 43 has two electrically steerable laser source-sensor assemblies 44 and 45, each with a laser source or transmitter 44a, 45a, respectively, and a laser sensor or receiver 44b, 45b. The laser assembly 44 is a high speed low resolution scanner used to generate a low resolution image to serve as a control map for the laser 45, which is a high resolution scanner that generates data that forms the three-dimensional model 26 used for tooth finish position calculation and appliance design and manufacture. The low resolution laser of the laser assembly 44 may be, for example, a laser scanning unit of the type manufactured by Keyence of Japan model LK031, while the high resolution laser 45 may be, for example, a laser scanning unit of the type manufactured by Keyence of Japan model LK081. The low resolution laser 44 is preferably set to produce three orthogonal coordinate measurements of points at a density of about two (2) data points per linear millimeter in each of three dimensions, while the high resolution laser 45 is preferably set to produce three orthogonal coordinate measurements of points at a density of about ten (10) data points per linear millimeter in each of three dimensions.

The input computer 30a is connected to the laser unit 43 to control its operating parameters and to interpret, format and store the 3-D data being generated. The computer 30a also steers the lasers 44 and 45 and orients the respective lower and/or upper halves 21, 23 of the physical model 20. For scanning, the halves of the model 20 are individually mounted in a holder or support 46, which is mounted to an inner yoke 47 so as to rotate thereon on its axis under the control of a servo motor 48 which is controlled by the input computer 30a. Similarly, the inner yoke 47 is pivotally mounted to an outer yoke 49 to pivot on an axis that is perpendicular to the axis of rotation of the holder 46 and located to approximately intersect the half of the model 20 that is mounted on the holder 46. This allows the model half to be oriented at any angle desired with respect to the laser scanner 43 so that direct line-of-sight views of the model can be obtained by the lasers of all surface areas of the model. The outer yoke 49 is controlled by a servo motor 50, which is also controlled by the input computer 30a.

The outer yoke 50 is mounted to a carriage 51 that is movable horizontally on a table 52 on two axes by servo motors 53,54, respectively, both of which are controlled by the input computer 30a. The laser assembly 43 is also mounted on the table 52. The movable carriage 51 allows for precise placement of the half of the model 20 in the holder 46 at a distance from the laser 43 for optimal focusing and for the optimal angle of incidence of the laser on the model half being scanned. The yokes 47 and 49 and the carriage 51 are preferably made of heavy metal castings and the table 52 is preferably made of heavy granite blocks supported on a solid foundation so that vibrations that can affect the precise scanning of the high resolution laser 45 are not transmitted between the laser scanner 43 and the holder 46.

Figure 3A:
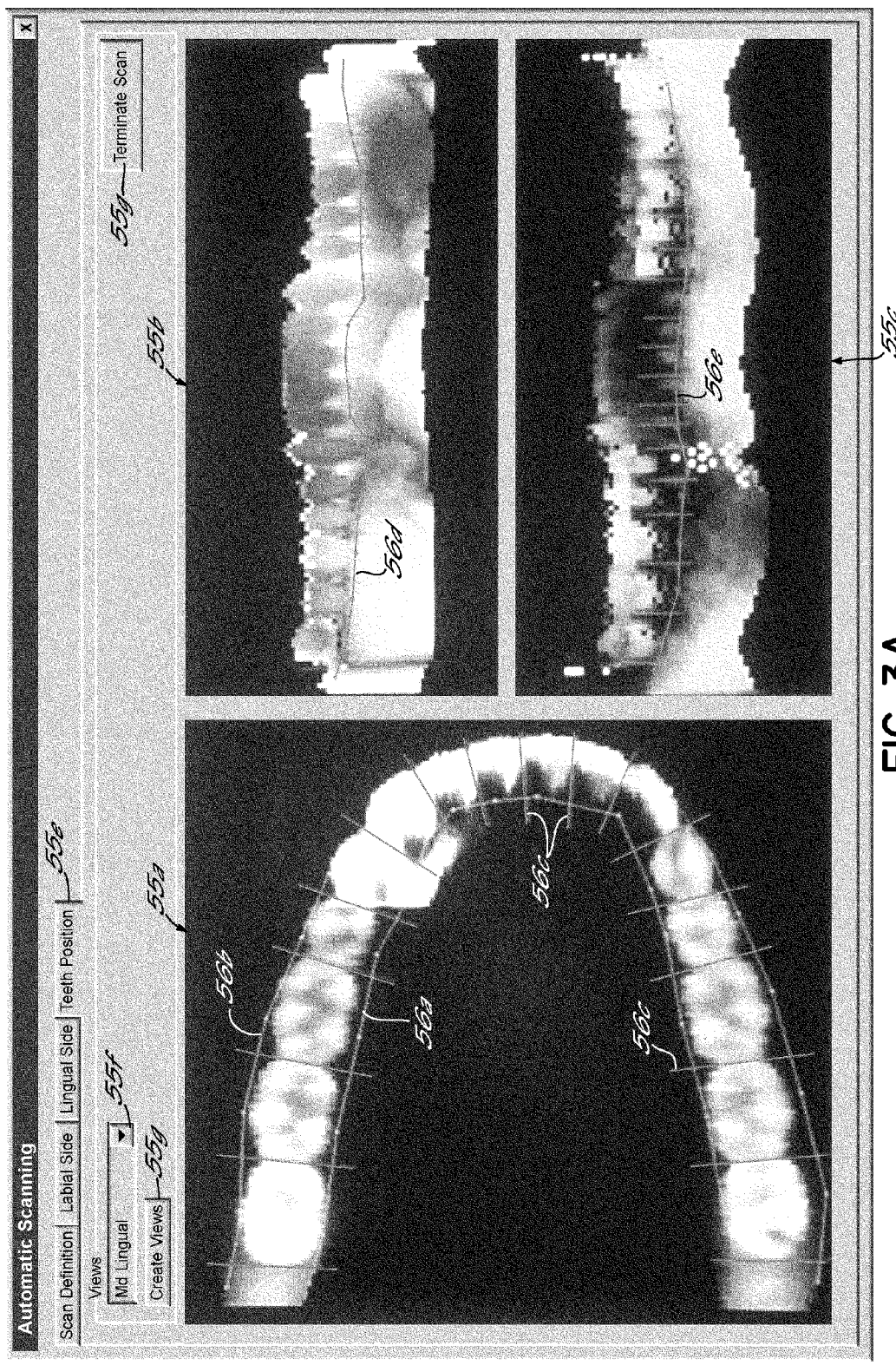
FIG. 3A is a representation of the display produced by the computer of the scanner of FIG. 3 illustrating three views of a low resolution scanned image of a model of a patient's lower dental arch.

When the scanner 33 is operated, the operator 28 sets up the scanner parameters through a setup screen at the computer 30a and initiates low resolution scanning of the lower jaw model half 21. For the low resolution scanning, the model 21 is placed on the holder 46 and the inner yoke 47 is oriented by computer controlled operation of the motor 50 so that the low resolution laser 44 scans a top view of the model 21 which is displayed on the monitor of computer 30a as illustrated in the left window 55a of FIG. 3A. The computer then reorients the yoke 47 to generate low resolution views of the labial and lingual sides of the teeth, by rotating the model 21 in the holder 46 on the inner yoke 47 by the computer controlled operation of the motor 48. This produces low resolution panoramic lingual views represented by the windows 55b, 55c, respectively. The views 55a, 55b, 55c are effectively two dimension displays generated for the purpose of providing the operator 28 with a way to define the location of the various teeth of the model 21 in the three-dimensional space at the scanner 33.

Controls are provided at the top of the screens of the display of the computer 30 that are relevant to the operation being performed or the data being viewed. These controls include a menu, for example, menu 55e, that expands or changes as different selections are enabled in the course of the setup as well as a control 55f for selecting various views and command buttons 55g for actuating various calculations or initiating equipment functions.

Figure 3B:
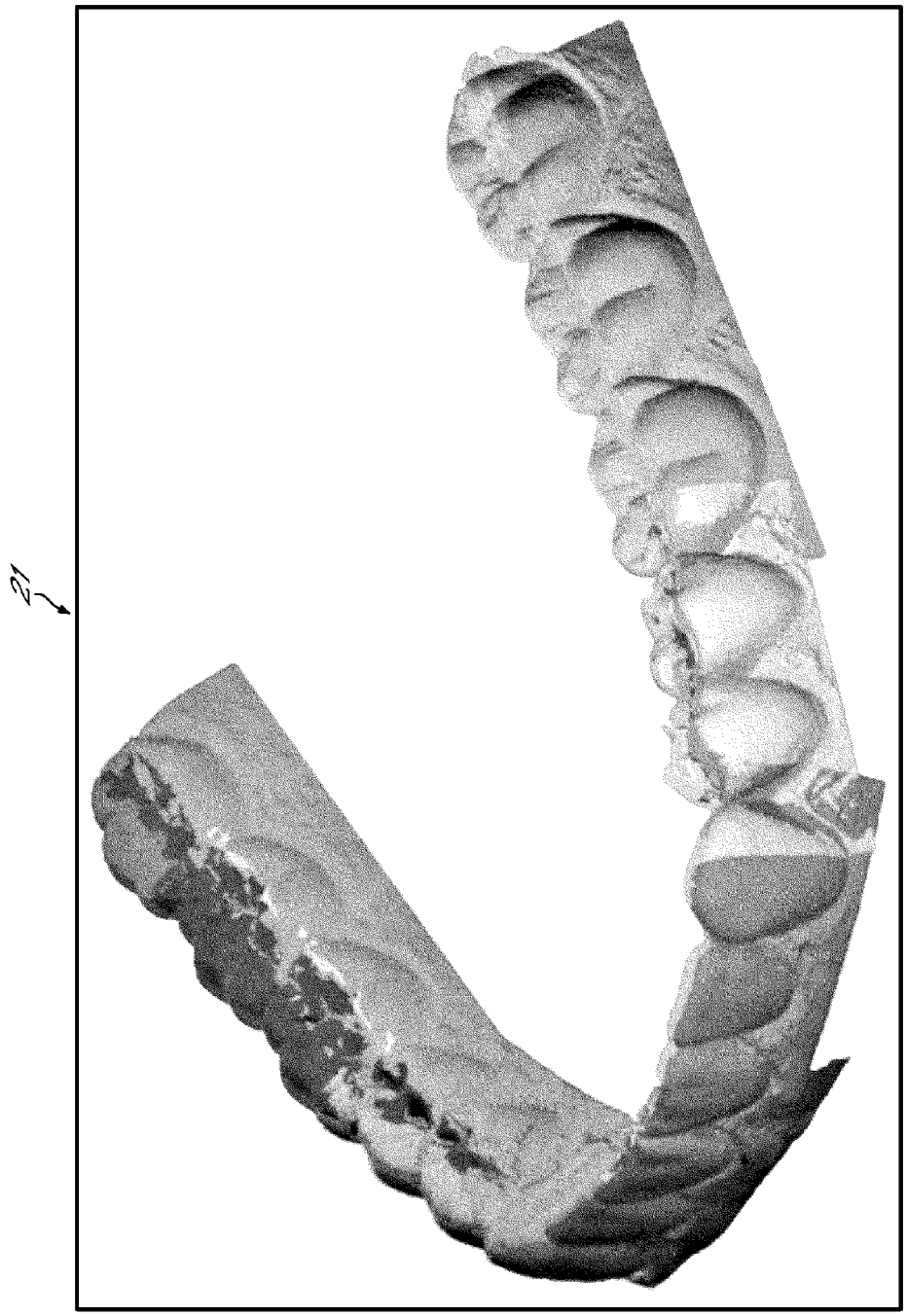
FIG. 3B is a computer display of perspective representation high resolution data scanned by the scanner of FIG. 3 from a model of a patient's lower dental arch.

At the terminal of the input computer 30a, the operator 28 can use a pointing device to select points on the computer screen to define the inner and outer boundaries 56a and 56b, respectively, of the lower jaw, and lines 56c separating the individual teeth, from the top view 55a, so that each tooth can be represented as a separate three-dimensional object. The lines 56c may be automatically displayed on the elevational views 55b, 55c, on which the operator 28 can further select points to define labial and lingual tooth-gum lines 56d and 56e, respectively. Once the boundaries 56a-56e are defined from the view screens 55a-55c, high resolution scanning can be initiated with the high resolution laser 45. High resolution scanning uses the boundary lines 56a-56c to precisely aim the laser 45 and thereby minimize the amount of data generated. The laser 45 generates up to fifty or more segmented high resolution images of different and overlapping areas of the model 21, a composite screen display of which is illustrated in FIG. 3B. The data points are each defined by three orthogonal x,y,z coordinates. The separate images are each stored in separate data files. Once the separate image data files are generated, the images can be knitted together by the use of conventional software available for that purpose to produce a single three-dimensional high resolution digital mandibular model of the patient's lower jaw with the teeth of the patient. Initially, this is possible for the teeth in their pretreatment maloccluded positions. As tooth finish positions or other treatment positions are calculated, as described below, the composite images can be displayed to show teeth in any of such positions. FIG. 3B is a composite image of teeth in ideal positions. Standard software is available that includes various three-dimensional image processing programs and data conversion files provided with available laser scanning devices, to produce image files in standard data formats. The maxillary tooth model 23 is similarly produced.

When the three-dimensional low and high resolution data files have been produced and stored by the input computer 30a with data of separate three-dimensional shapes of each of the patient's teeth as well as vector data locating and orienting each tooth shape model in its maloccluded pretreatment position relative to a reference that locates the teeth relative to each of the others, the files are ready for further processing in designing the patient's occlusion by calculating or otherwise determine finish position and then designing a custom appliance to move the teeth to positions dictated by a treatment plan. The data files are loaded into the computer 30, which may be a separate analysis and design computer 30b, which is programmed to produce, under the interactive guidance of an operator 28, and interactive involvement of the orthodontist 14, a three-dimensional digital model of the teeth of the patient in some proposed posttreatment position. In doing so, an initial proposed treatment position is calculated by the computer 30b and presented for review by the orthodontist 14. This electronic model, once modified and approved, serves as the basis for the design of the custom orthodontic appliance that moves the teeth to the positions represented in the model.

In the analysis and design computer 30b, the data are filtered or processed to extract the geometric characteristics from the three-dimensional images that are to be used to calculate the final positions of the teeth and to design the appliance. The extracted information defines a simplified digital model of the teeth, and preferably also includes parameters customarily used by the orthodontist to define or describe tooth position, such as torque, tip and rotation angles, and may also include X,Y,Z displacements from some reference point, plane or archform. Typically, the three-dimensional high resolution digital model is in the form of a 3-D bitmap or raster image where the simplified model is in the form of a vector image file, overlay or layer of the bitmap or raster image.

Figure 4:
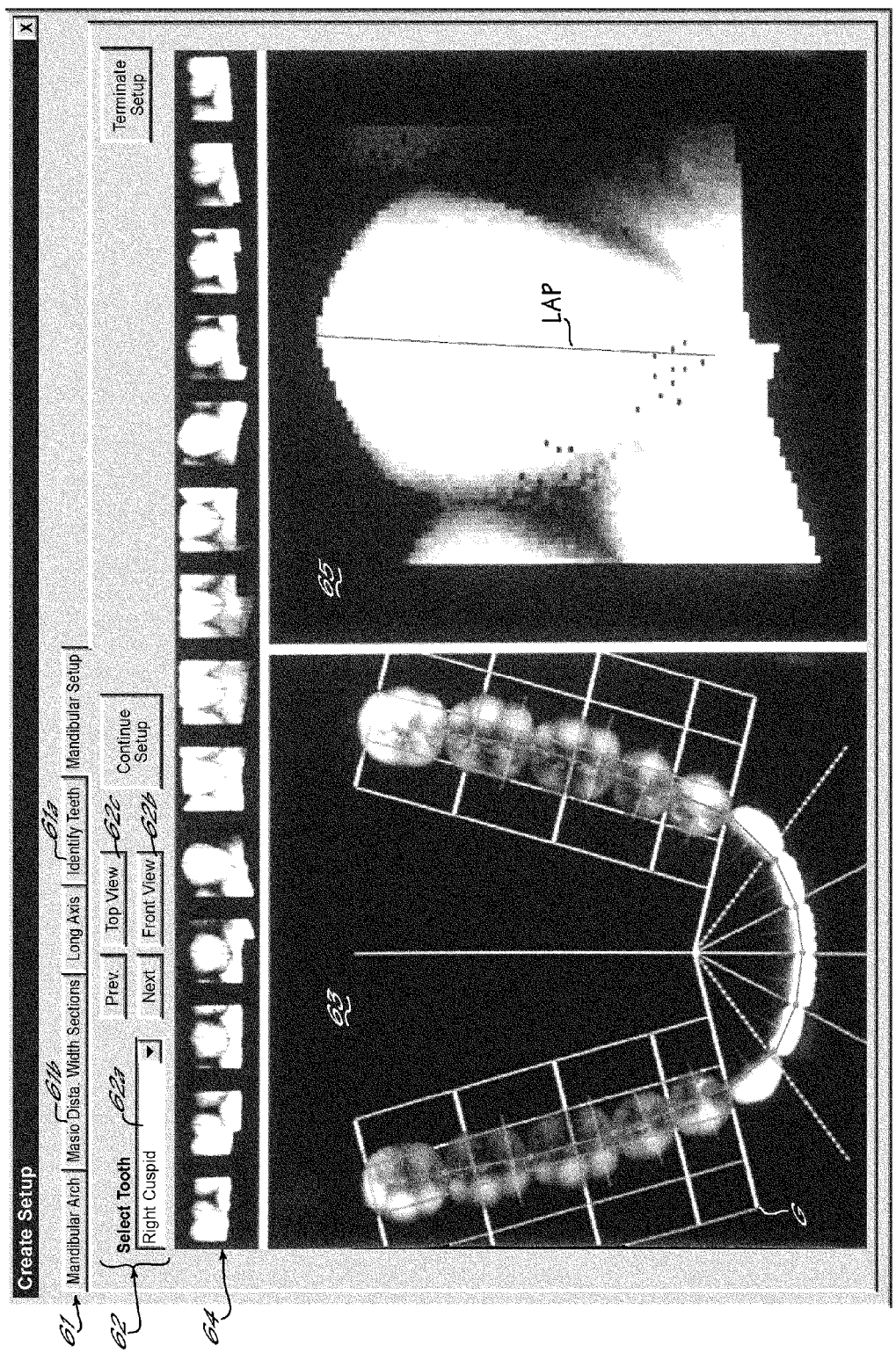
FIG. 4 is an illustration of a display of the appliance facility computer of the system of FIG. 1 displaying an initial setup screen.

The generation of the simplified data image is initiated by an operator 28 of the analysis and design computer 30b by selecting a menu option, for example that named "Create Setup", which appears on the main menu bar at the top of the screen when adequate data to calculate tooth treatment positions is available in the computer. The "Setup" is a term often used to refer to the finish, target or posttreatment positions of the teeth that are the objectives of the treatment plan. Selecting the "Create Setup" option displays a screen 60, an example of which is illustrated in FIG. 4. The screen 60 is divided into a main menu 61, sets of option buttons 62, one associated with each of the items on the main menu 61, an archform window 63, which displays an occlusal plan view of one of the mandibular or maxillary arches, a tooth icon bar 64 which displays an icon in either occlusal or labial view of each individual tooth in the arch in the window 63, and a selected tooth window 65, which displays an enlarged view of a selected one of the teeth of the arch shown in the window 63. In the Create Setup mode, the computer 30b steps through a series of procedures in which the shape of the patient's lower jaw is determined and characteristic geometric features of the patient's teeth are extracted from the three-dimensional digital model. The procedures are capable of being performed either automatically with the computer 30b making decisions, or interactively with an operator 28 and the program of the computer 30b contributing to decisions. The procedures are explained in the interactive or semi-manual mode for simplicity, but the decision making processes that are explained can be made automatically using coding the described steps in programmed algorithms.

The Setup mode starts with the setup of the teeth of the mandibular arch. As the Setup mode steps through its procedures, the number of items on the main menu bar 61 increases or otherwise changes so that the operator can select from among all current available procedures or return to view the data displays that can be generated from data produced by completed procedures. This facilitates the entry of data in the proper sequence. An initial procedure of the mandibular setup is the defining of the mandibular arch in the form of a generally arch-shaped mathematical function that represents the centerline of the trough in the patient's lower jaw bone containing the roots of the mandibular teeth. This function is provided to satisfy the first condition of the proposed tooth finish position calculation: that the patient's mandibular teeth should be contained and aligned within the cancellous portion of the patient's mandibular bone. The function can be considered a mathematical representation of the patient's mandibular skeletal archform.

Figure 4A:
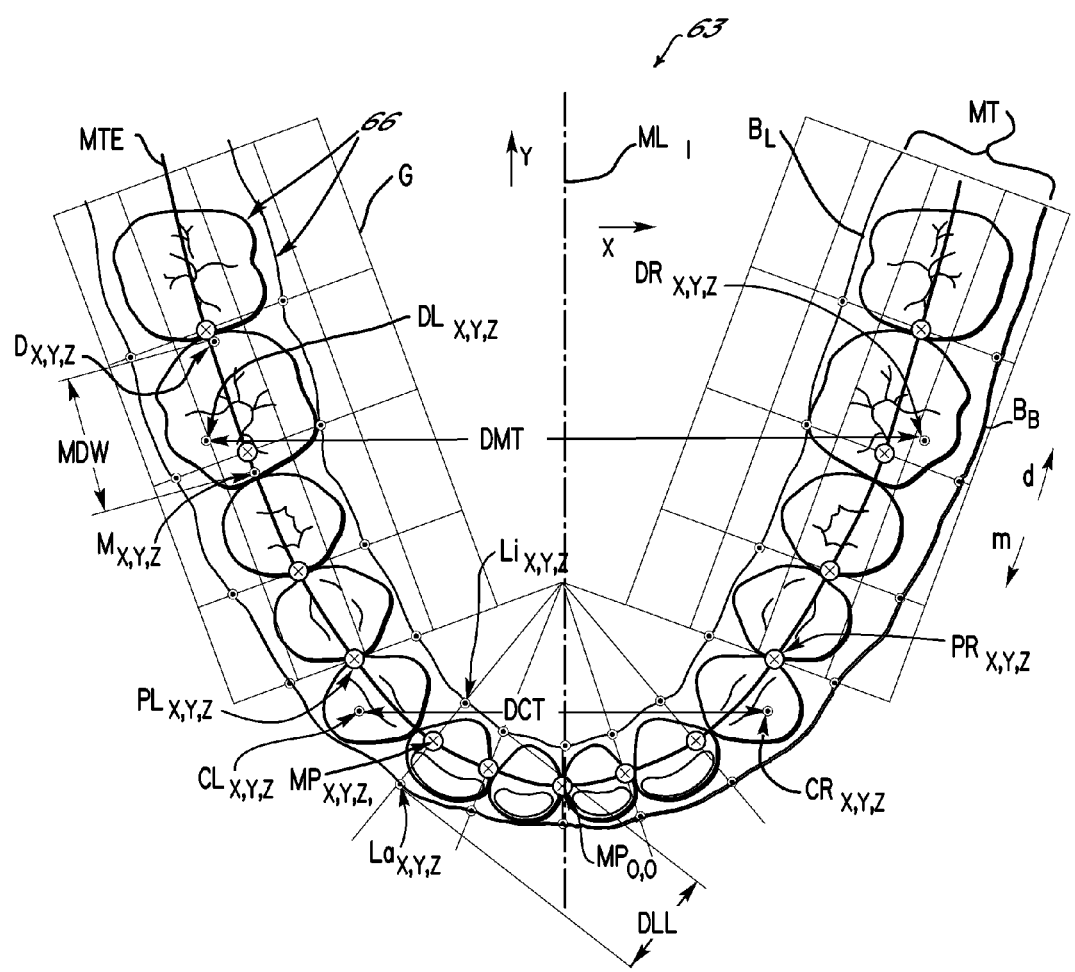
FIG. 4A is a diagram of a portion of the setup screen of FIG. 4.

To generate a function defining the mandibular skeletal archform, an occlusal view 66 is displayed in the window 63 of the patient's mandibular arch from the high resolution digital model, as illustrated in FIG. 4A, from which an outline of tissue covering the mandibular bone structure defining the mandibular trough MT is visible. The digital bitmap image 66 is overlaid with a computer generated positioning grid G. The computer 30b may pause at this point to allow the operator 28 to adjust the position of the grid G. The grid lines intersect the boundaries of the mandibular trough. These boundaries $B_B$ and $B_L$ can be selected by pattern recognition software, manually by the operator 28 clicking with a pointing device at the grid and boundary intersection points, or first with software and then allowing the operator 28 to confirm or modify the software selections. The selection defines three-dimensional Cartesian coordinates $La_{X,Y,Z}$ and $Li_{X,Y,Z}$ of labial and lingual limits, respectively, of the cortical bone of the patient on both sides of the jaw, the data of which include a third Z dimension, derived from the three-dimensional model, of each point that is selected on the two dimensional display. Once the intersection points of the mandibular trough boundaries and the grid are defined, the computer 30b calculates midpoint coordinates $MP_{X,Y,Z}$ between each of the individual labio-lingual pairs of La and Li. Also calculated are the bone width distances DLL between each of the respective labio-lingual pair La and Li. The midpoints $MP_{X,Y,Z}$, one of which is the designated origin $MP_{0,0,0}$ at the midpoint of the jaw, lie on an arch that describes the size and shape of the center of the cancellous portion of the mandibular bone. From this a mandibular trough equation MTE is derived, from which a symmetrical equation SMT may be derived.

Then, additional procedures are carried out, first for the mandibular teeth then for the maxillary teeth. These include refining the boundaries of each of the teeth from the archform images so that their images can be independently moved in the computer, selecting the widths of the teeth across the teeth from their points of contact with adjacent teeth on the same arch, selecting landmarks or tooth prominences, including incisal edges, cusps, grooves and ridges, and defining the crown long axes of the teeth, all in three dimensions. All of these procedures can be carried out using pattern recognition programming techniques. The accuracy of each procedure will benefit by allowing manual confirmation or correction of computer selected parameters and landmarks by an operator 28.

Figure 4B:
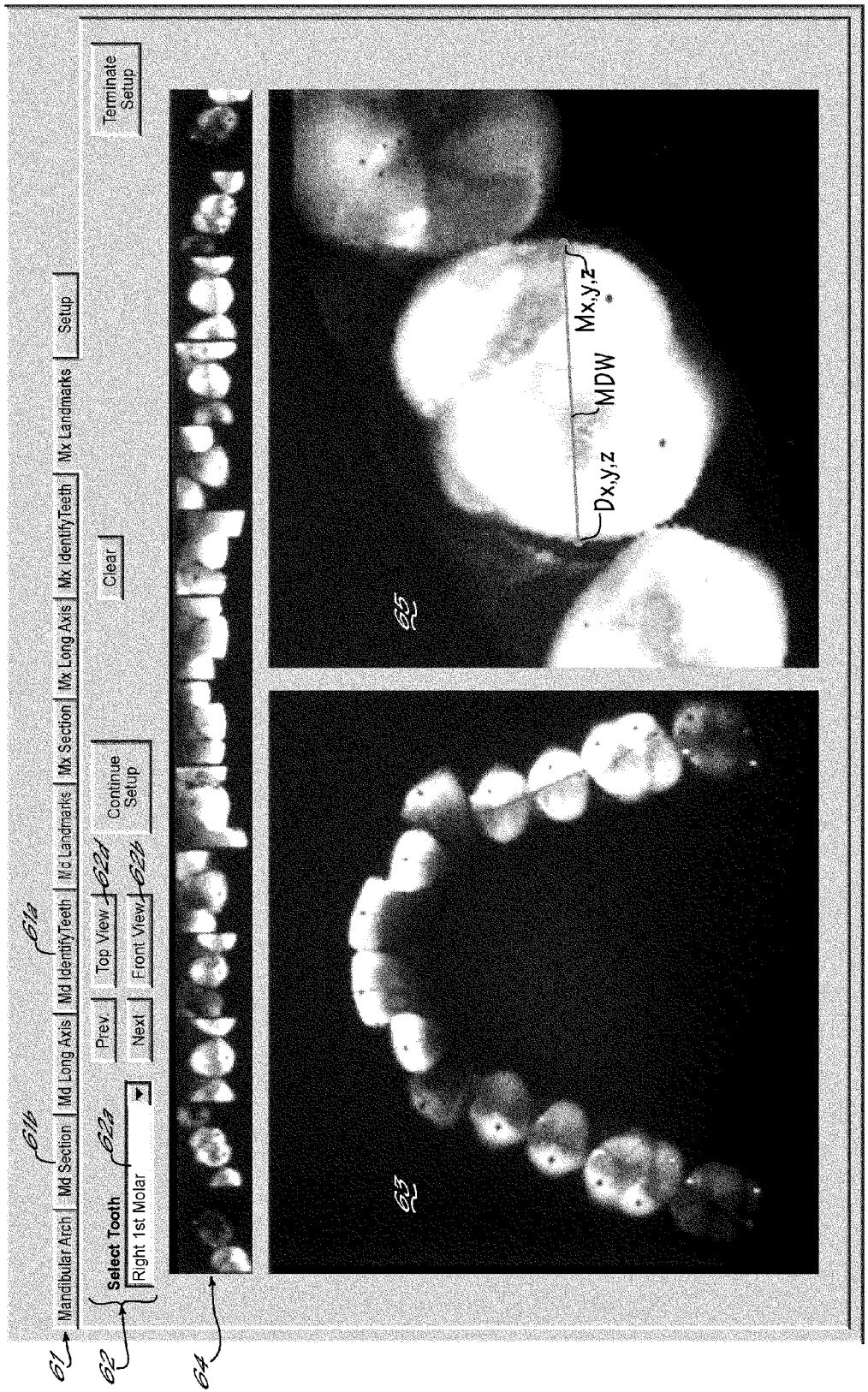
FIG. 4B is an illustration of a display of the appliance facility computer of the system of FIG. 1 similar to FIG. 4, displaying another setup screen.

The teeth are identified with selection of menu tab 61a (FIG. 4), either automatically, or by operator selection. The tooth identification procedure tells the computer, or confirms for the computer, a determination made by an operator or the computer that a particular portion of the three-dimensional data represents the shape of a particular tooth. Tooth identification can proceed, automatically by the computer 30b and/or manually by the operator 28. For example, the selection can be made with a selection by the operator 28 of areas of the image in window 63 as the names of the individual teeth are sequentially displayed in a box 62a, or by the operator confirming images sequentially displayed in the window 65 as corresponding to the tooth names displayed in the box 62a as shown in FIG. 4B, or by the program in the computer 30b making the determination for each of the teeth. Whether to make manual selections or to view automated selections, the operator 28 can choose windows 64 or 65 to display occlusal views or facial views of the individual teeth by clicking on buttons 62b or 62c.

Next, the distances between the mesio-distal extremities, or mesio-distal widths MDW, of each of the mandibular teeth are defined with selection of menu tab 61b. This width is the distance between the contact points which a tooth will have with adjacent teeth when the teeth are arranged in contact with each other in a dental arch in their treated or finish positions. In addition, the sum of the mesio-distal widths of the teeth on a dental arch constitutes the total length of the dental arch. The widths, once determined, are added together to determine the total length of the dental arch and the amount of space needed if all of the teeth at their original dimensions of the patient are to be retained. The mesio-distal widths can be determined either automatically by software using algorithms to recognize and interpret the teeth from the three-dimensional data and interpreting the mesial and distal contact points of the teeth with adjacent teeth, by the operator 28 manually selecting the tooth intersection points on occlusal views of the teeth as they are displayed in the window 65, or by the operator confirming selections made by the computer. For simplicity, the MDWs are illustrated with respect to the mandibular teeth in FIG. 4A, and the determination of these widths is carried out, for mandibular and maxillary teeth, using screens as illustrated in FIG. 4B for the maxillary teeth with the top view of the tooth selected for display in window 65.

More particularly, for both upper and lower teeth, MDWs may be interactively picked by the operator from the enlarged occlusal image 65 illustrated in FIG. 4B. With the MDW menu tab 61b selected for mandibular teeth, only occlusal views are available in the tooth icon bar 64 and for the enlarged individual tooth image window 65. The operator picks the mesial and distal contact points $M_{X,Y,Z}D_{X,Y,Z}$, respectively, for the tooth, which in the illustration is the upper left first molar. The points are selected by the operator by clicking a pointing device at a point in the X,Y plane as displayed in the window 65, whereupon the Z coordinate is determined from the high resolution data file image of the tooth. The computer 30b calculates the distance between these points and stores the X,Y component of this width, from the coordinates of contact points $M_{X,Y}D_{X,Y}$, as the MDW for the tooth. This width is defined in the data as a line in vector form in a way that is related to its location in relation to the three-dimensional data of the shape of the tooth.

In the Setup mode, the operator 28 visually selects points that locate the prominences of each of the teeth that serve as the landmarks that form the starting points for the calculations of tooth ideal or finish position calculations. In tooth position calculations, the computer 30b may use the selections directly, or may take into account actual three-dimensional data of the tooth surfaces so that the accuracy of the manual selection of the landmarks is not critical. In lieu of manual location of the landmark points and all other selections, the locations of the points may be done automatically by the computer through analysis of the three-dimensional tooth shape data of each tooth as well as of the adjacent teeth. Automatic selection may be presented for acceptance or change by the operator 28. This may be particularly useful in the case of teeth that are worn or damaged. Automatic selection seeks to locate the selected points with the same objectives as those described herein as done manually by an operator. The prominence landmarks selected in this way include the incisal center points of each of the anterior teeth, each of the cusps on the posterior teeth and each of the marginal ridges and central grooves on the posterior teeth, and each for both the upper and lower teeth. When manually selected, these selections are made from the occlusal view of the teeth displayed in the individual tooth image window 65 as illustrated in FIG. 4B and can be adjusted from a front view as illustrated in window 65 in FIG. 4 or in a mesial distal view as illustrated in FIG. 4C.

Figure 4C:
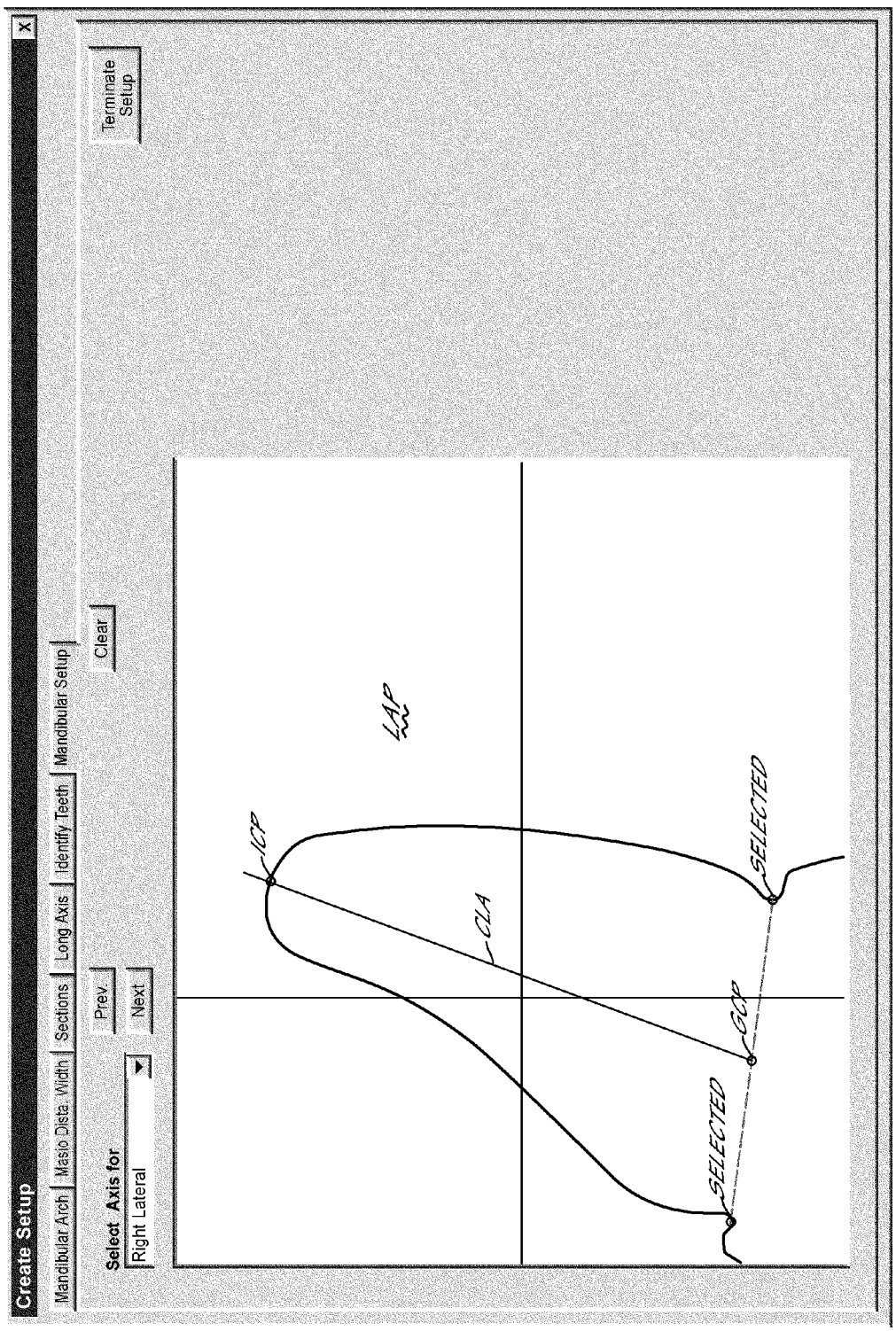
FIG. 4C is an illustration of a selected display window of the screen of FIG. 4B showing a tooth cross section in a crown long axis plane.

The operator 28 also selects points to define a crown long axis CLA of each tooth, which is most easily done in the first instance in a mesial-distal view, as illustrated in FIG. 4C. Definition of a crown long axis for a tooth can be achieved manually by the operator 28 selecting points to define a long axis plane LAP through the tooth. This selection is carried out, for example, by selecting two points on the facial view to define an orientation of a line in the long axis plane proximate the facial side of the tooth, and two points on the occlusal view of the tooth to define an orientation of a line in the long axis plane proximate the occlusal surface of the tooth. Usually, such points are the major prominences such as incisal center points or mesial buccal cusps and central tooth gum intersection points.

Preferably, the selection of points to define the plane LAP is made first by selecting a labial and lingual point from the plan or occlusal view of the tooth, as illustrated for example in the individual tooth image window 65 in FIG. 4B. Then with such an LAP plane defined, a mesial-distal view of the LAP plane as illustrated in FIG. 4C is displayed. From this view, gingival intersection points on the lingual and facial sides of the tooth can be selected, the midpoint of which, when calculated, defines a gingival center point GCP on the crown long axis of the tooth. The CLA is calculated to extend through this point through a predetermined one of the prominences of the tooth, depending on the type of tooth involved. When all of the selections have been made, the digital model of the teeth includes two types of files, one containing the high resolution, three-dimensional digital tooth shape data of each of the teeth arranged in their pretreatment positions and the other containing simplified vector data representations of the teeth, each formed of a long axis plane LAP with the crown long axis CLA located therein, and with the tooth's mesial distal width vector MDW and the various tooth landmarks of the tooth located in reference to the plane and the CLA. The torque and tip angles of each of the teeth can be calculated in reference to the orientation of the CLA relative to the occlusal plane or the plane of the MTE, and the rotation angle can be calculated from the orientation of the MDW about the CLA relative to the tangent of the MTE.

Figure 5:
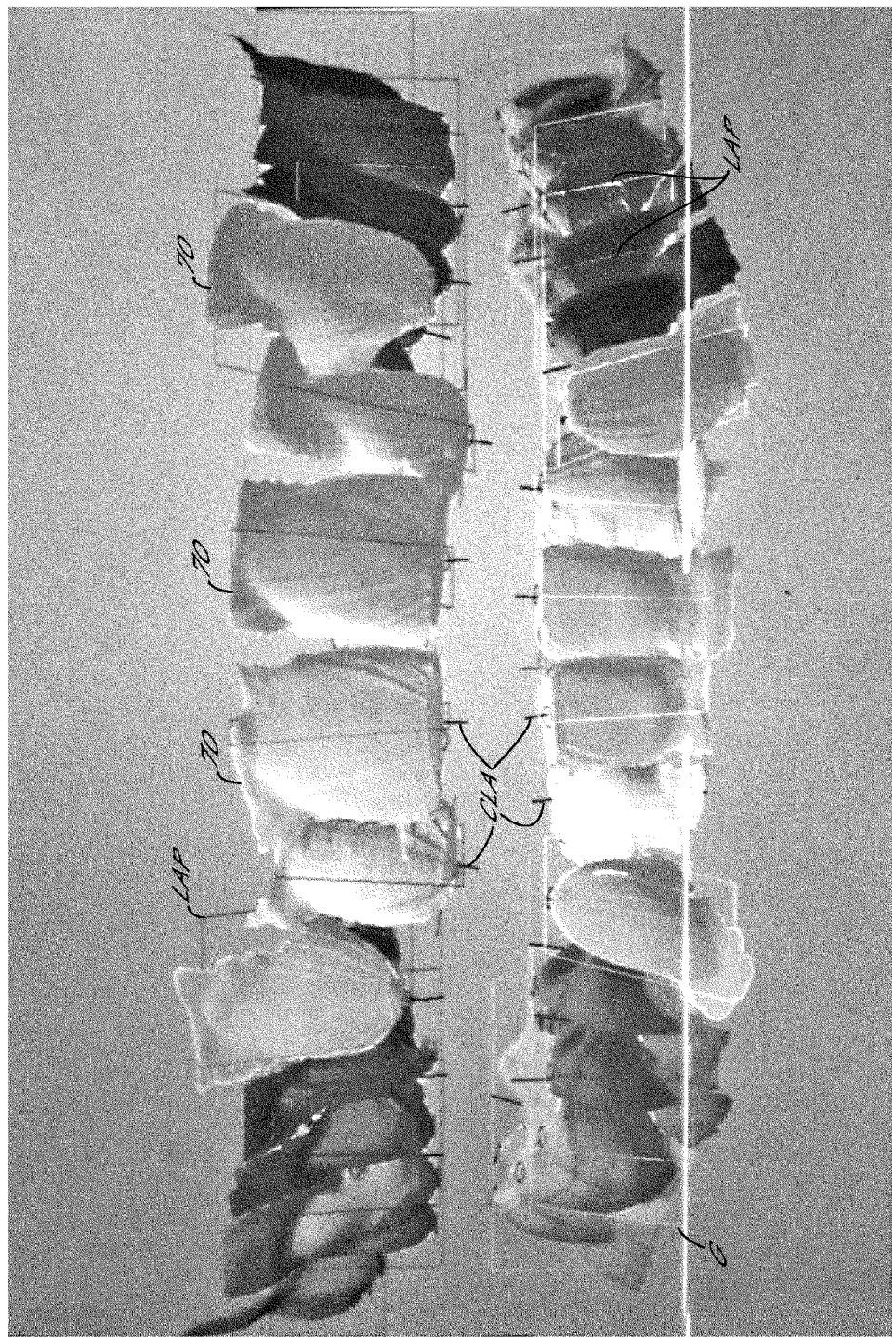
FIG. 5 is a display of the appliance facility computer displaying a perspective view of the patient's teeth, in high resolution, three-dimensional solid images, in their relative positions prior to treatment.
Figure 5A:
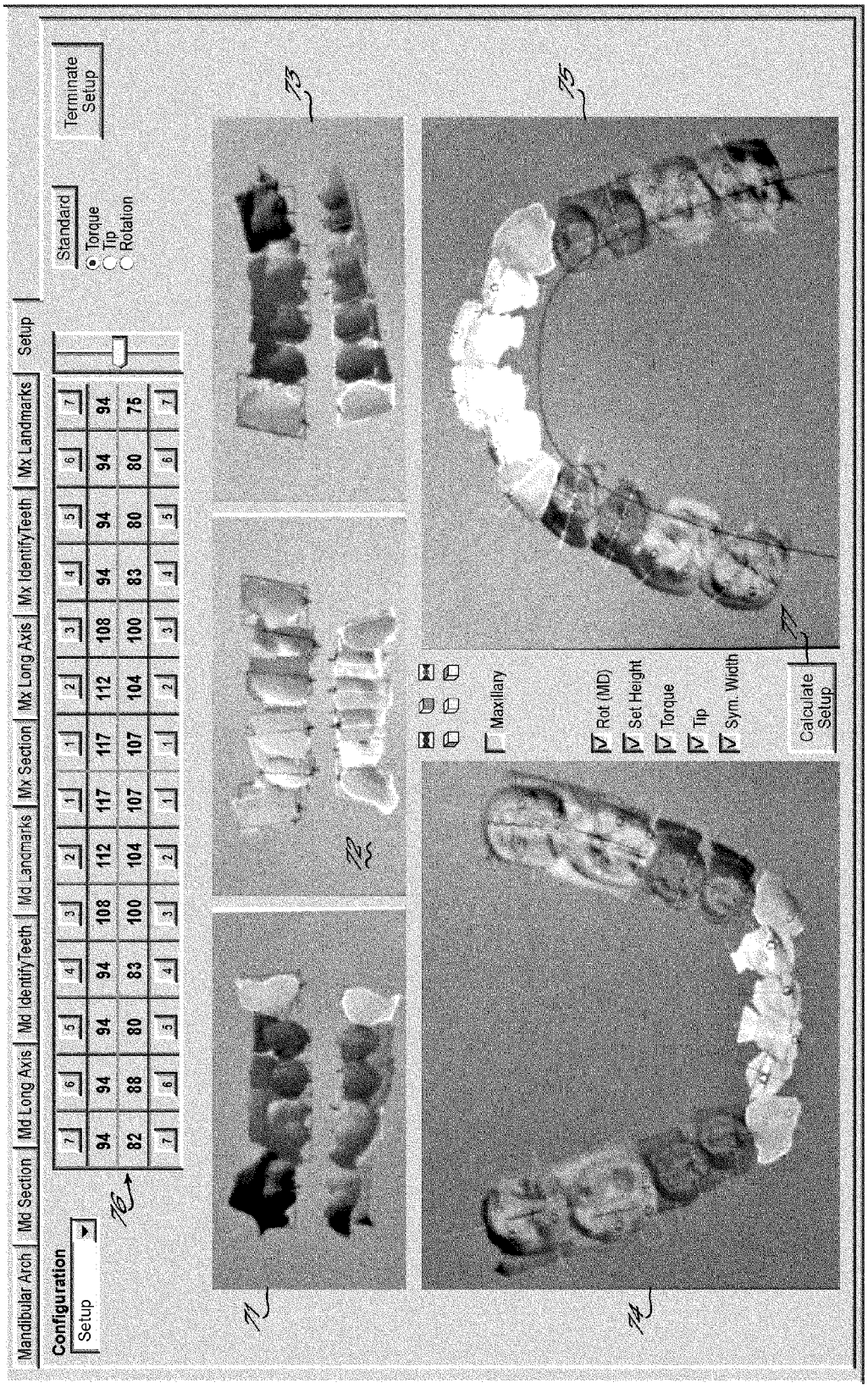
FIG. 5A is another setup screen display of the appliance facility computer displaying various view windows showing the teeth of the patient in their relative pretreatment positions of FIG. 5A.

To assist the orthodontist, a perspective view showing each of the teeth in their pretreatment positions is generated, as illustrated in FIG. 5. This view shows the three-dimensional solid shapes 70, produced from high resolution, three-dimensional data from the raster image file, of each of the teeth of both the upper and lower dental arches arranged in their pretreatment positions relative to each other. Each tooth is, preferably, illustrated in a different color. Three-dimensional information can be displayed in several ways, one being by the use of brightness variations to represent the dimension perpendicular to the screen, or by shadow shading, or both. Stereoscopic techniques may also be made to produce three-dimensional viewing, for example, using color separation and goggles for the user. Holography can also be used for the three-dimensional displays. In the screen displays illustrated, superimposed on the solid images of the teeth are data from the simplified vector image file, showing the long axis planes LAP, the crown long axes CLA, and the grid G containing the equation of the mandibular trough MTE. A user can toggle between the view of FIG. 5 and the screen of FIG. 5A, which displays right, left and front views, as well as occlusal views of each of the arches, in separate view windows 71-75, along with a table 76 listing values for the torque, tip and rotation angles of each tooth.

Figure 5B:
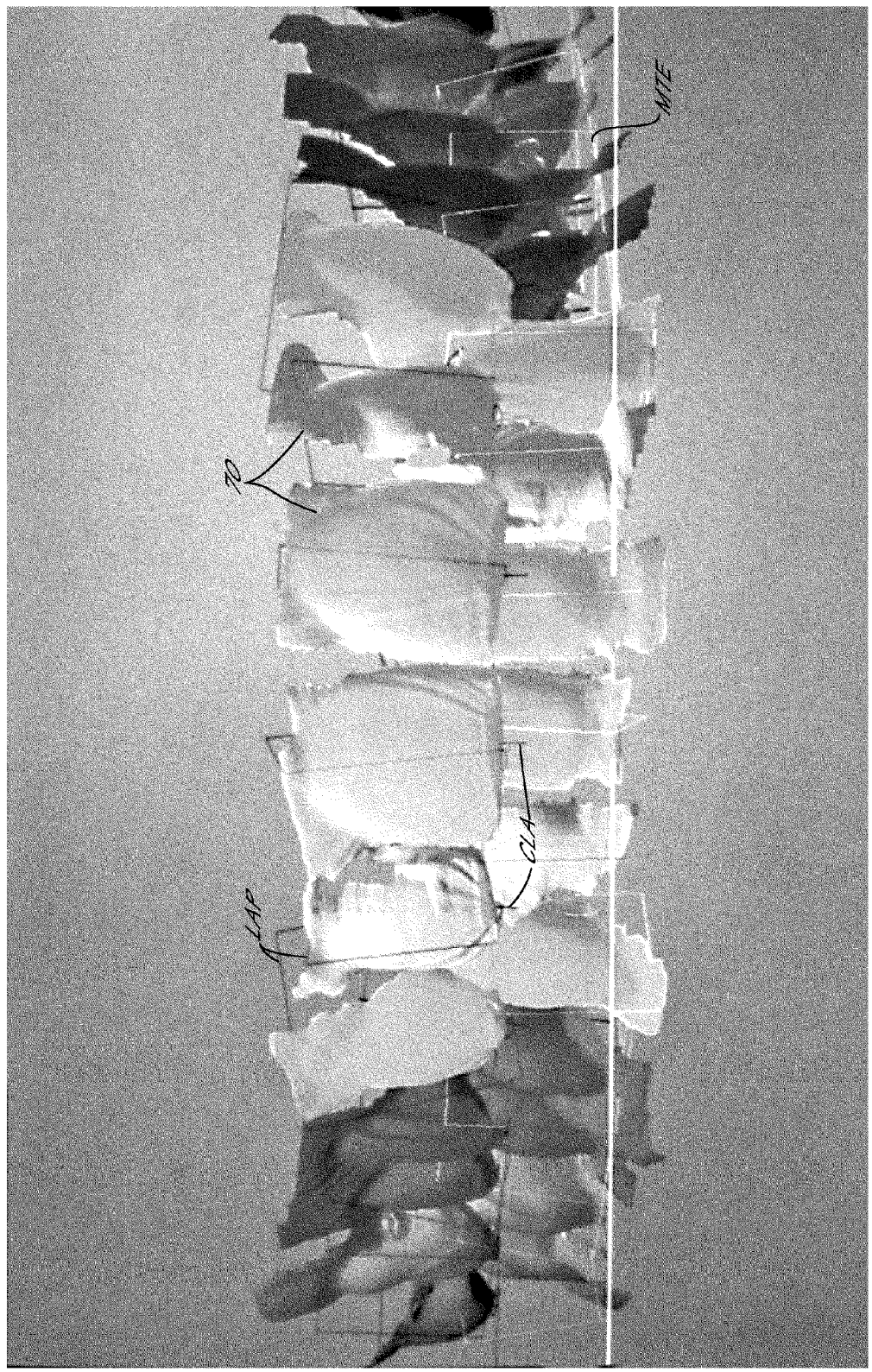
FIG. 5B is a display of the appliance facility computer, similar to FIG. 5, displaying a perspective view of patient's teeth, in high resolution, three-dimensional solid images, in calculated proposed relative posttreatment positions.
Figure 5C:
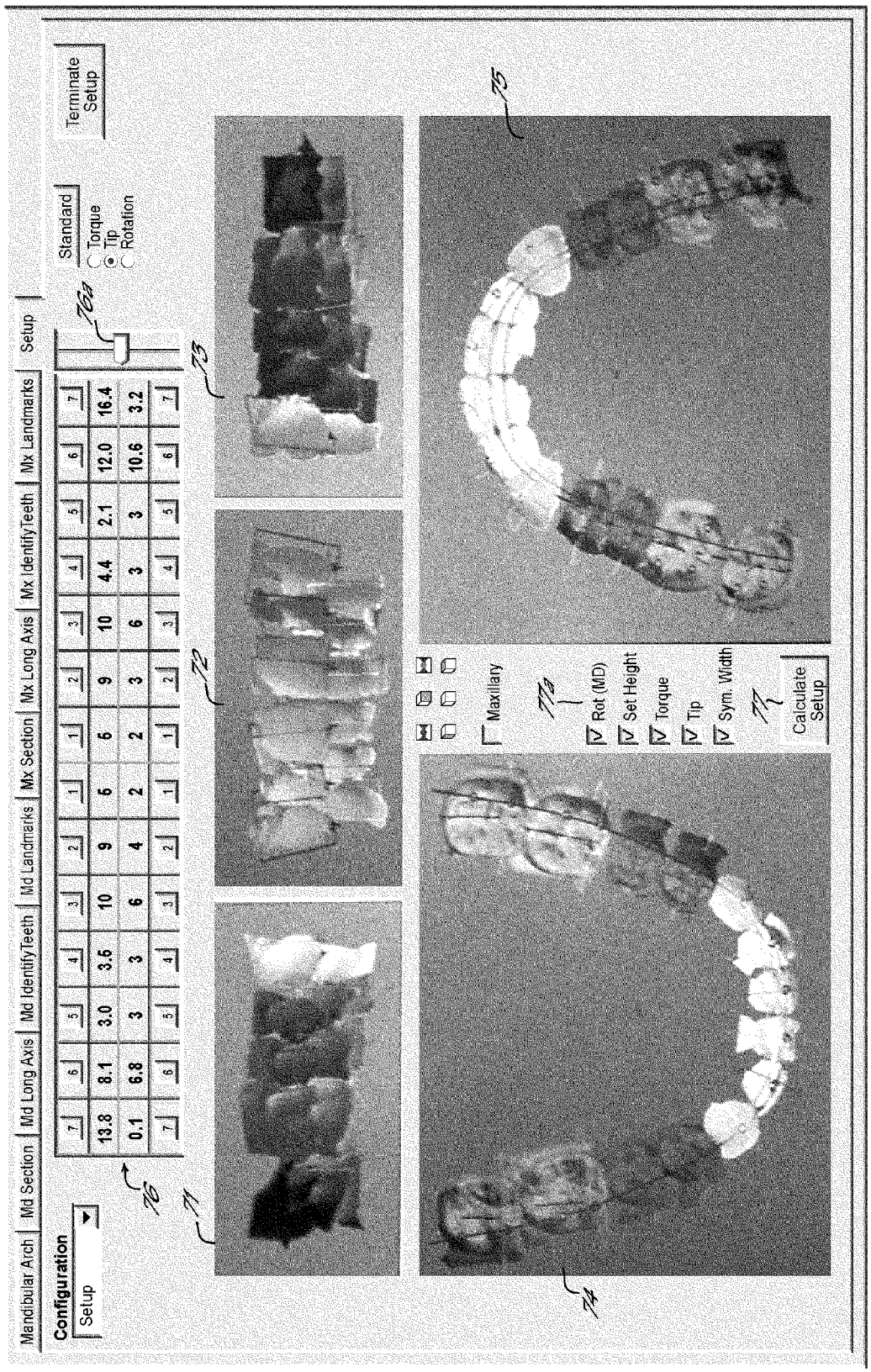
FIG. 5C is a display of the appliance facility computer, similar to FIG. 5A, displaying various view windows showing the teeth of the patient in the relative posttreatment positions of FIG. 5B.

The Setup mode ends with the tooth treatment position determination, or Setup Calculation. In this phase, suggested tooth finish positions are calculated and communicated to the orthodontist to adjust and approve prior to the design of the appliance, and then recalculated in accordance with the interactive communications between the orthodontist 14 at the office 11 and the design computer 30b at the appliance manufacturing facility 13. On the screen illustrated in FIG. 5A, an operator or the orthodontist can select a Create Setup button 77 and cause the computer 30b to calculate tooth finish or posttreatment positions, which can all be displayed together in a perspective view as illustrated in FIG. 5B, which is similar to FIG. 5, or as separate elevational or occlusal views as illustrated in FIG. 5C, which is similar to FIG. 5A, in which the values of the calculated posttreatment angles are numerically displayed in the table 76.

Tooth finish positions may be calculated by the methods described in the related patents and applications identified above, for example, in U.S. Pat. No. 5,431,562, to which are added the three-dimensional capabilities described herein. The calculations may take into account skeletal, maxillary and mandibular criteria, including occlusion, in determining the treatment positions of the teeth. In the calculations, the mandibular teeth, which should be contained and aligned within the cancellous portion of the mandibular bone, are translated horizontally so that their crown long axes are initially placed on the mandibular trough equation MTE. The buccal cusps and incisal tips of the mandibular teeth are made to align incisogingivally to produce a substantially flat mandibular occlusal plane, and are arranged in a smooth archform in which the buccal cusps align buccolingually with the central grooves of the maxillary teeth. The marginal ridges of the maxillary posterior teeth are arranged on the archform as the centric stops for the buccal cusps of the mandibular teeth. The central grooves of the maxillary posterior teeth define buccal lingual locations of the centric stops of the mandibular teeth. The calculations are all carried out in three dimensions.

The calculations of final treatment positions includes calculation of the positions of the teeth in three-dimensional coordinates as well as three orientation angles. The angles calculated are the torque angle or inclination, the tip angle or angulation, and the rotation angle. The torque angle is the angle of the tooth relative to the vertical in the facial-lingual/vertical plane, with the vertical direction being essentially that direction perpendicular to the occlusal plane. The tip angle is the angle relative to the vertical in a mesial-distal/vertical plane. The rotation angle is the angle of the defined plane LAP with a facial-lingual line about a vertical axis. Initial rotation angle calculations of the posterior teeth orient the teeth so that a line from the mesial-buccal cusp to the distal marginal ridge of the tooth is mesial-distal, that is, is parallel to the archform equation. Calculation of tip angle takes into account accepted norms and any prescription by the orthodontist as well as adjustments to best fit the three-dimensional surfaces and landmarks of occluding teeth at the occlusion while fitting the teeth with each other in their respective arches and supporting bone.

Figure 5D:
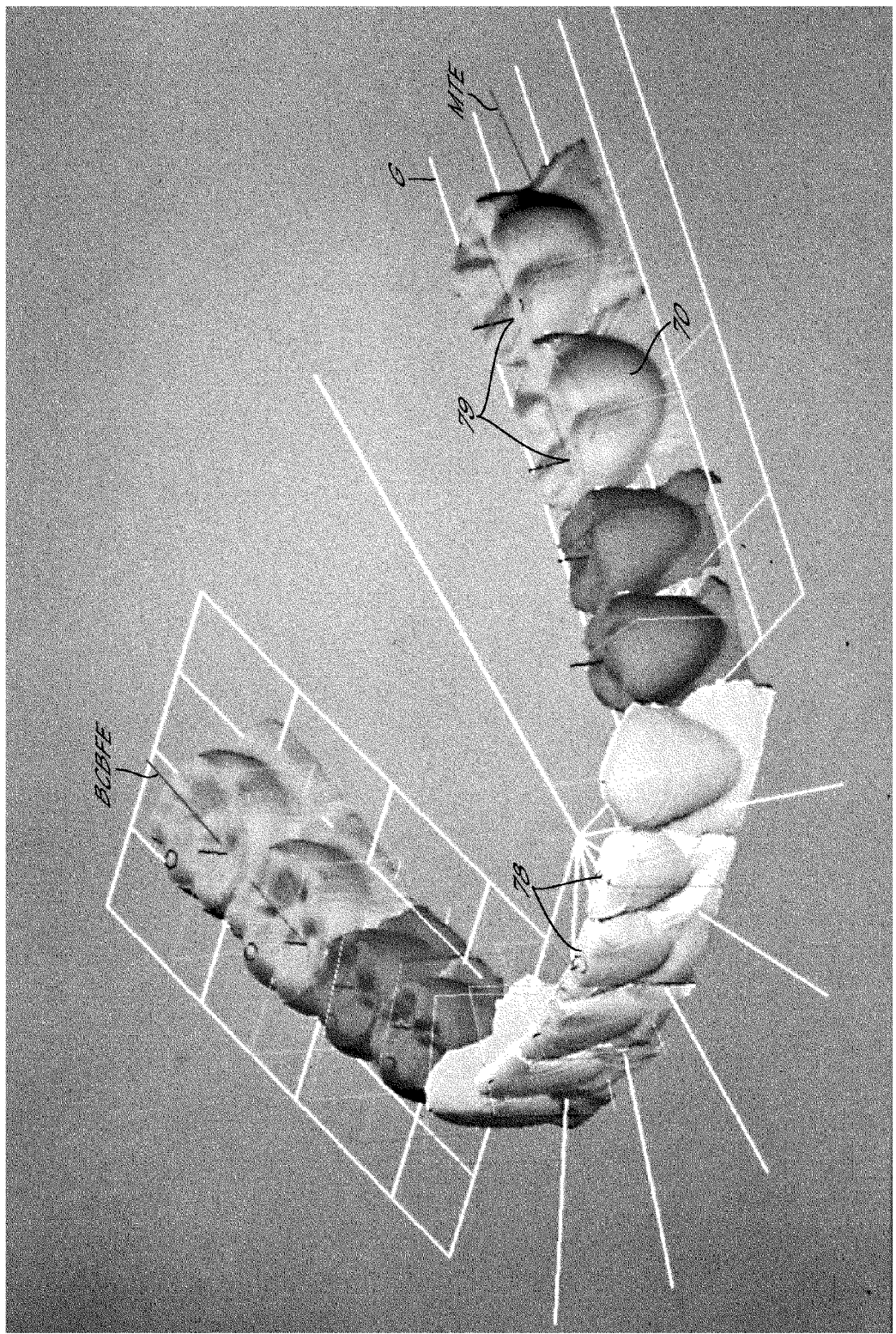
FIG. 5D is a display of the appliance facility computer displaying a perspective view of the mandibular teeth of a patient in the posttreatment positions of FIGS. 5B and 5C shown in solid three-dimensional images with simplified vector representations superimposed thereon.

In viewing the calculated finish positions, a user may view perspective displays of the teeth of a single arch, as in FIG. 5D which shows both the high resolution 3D data and the simplified vector data. The 3D solid images and the simplified vector representations of the teeth may be viewed separately or together. In the vector data file, various landmarks may also be displayed, as, for example, in FIG. 5E where the incisal tips 78 and buccal cusps 79 of the lower teeth are illustrated, which landmarks may serve, for example, as the reference points on the teeth for aligning the lower teeth on a best fit equation for the lower arch, such as the best fit buccal cusp equation BFBCE that is described more fully in the related patents.

The person viewing the display can communicate feedback information regarding the suggested tooth positions and orientations toward which the teeth of the patient are to be moved by orthodontic treatment, which can include information of changes to the suggested tooth positions and orientations or information in the form of change data from an orthodontic practitioner indicating selected changes in the suggested tooth positions and orientations. For example, in viewing the calculated finish positions that are suggested by the computer 30b, the orthodontist 14 can adjust the positions of any of the teeth in six degrees of freedom on a computer at the orthodontist's office 11 which is connected to the computer 30b at the appliance design facility 13 through a telephone or wireless link or other network. Normally, an orthodontist first considers adjustments to the torque, tip and rotation angles of the teeth. The angle adjustments are made by selecting the angle and tooth to adjust in the table 76 (FIG. 5C) and then to adjust a slide control 76a or type in a new value for the angle to be adjusted. As the value changes, the display changes to reflect the change in the value being made. The orthodontist can also adjust any tooth in x,y,z coordinates or in gingival-occlusal, facial-lingual and mesial-distal coordinates. Rather than translating the entire tooth, which presents interference issues, the orthodontist might adjust particular landmarks. When the adjustments have been made by an orthodontist and a testing of the changes made is desired, the orthodontist selects the Calculate Setup button 77 to cause the computer 30b at the appliance design facility to recalculate the treatment positions of all of the teeth based on the changes made by the orthodontist. In doing so, the orthodontist can select or unselect, in check boxes 77a provided, the parameters that can be changed in the setup calculation. In this way, the orthodontist can also test extractions by selecting the elimination of selected teeth from the calculations, and may test over-corrections that the orthodontist might desire. The setup recalculations proceed according to the orthodontists selections to position the teeth in stable positions according to predetermined criteria stored in the computer 30b.

Figure 5E:
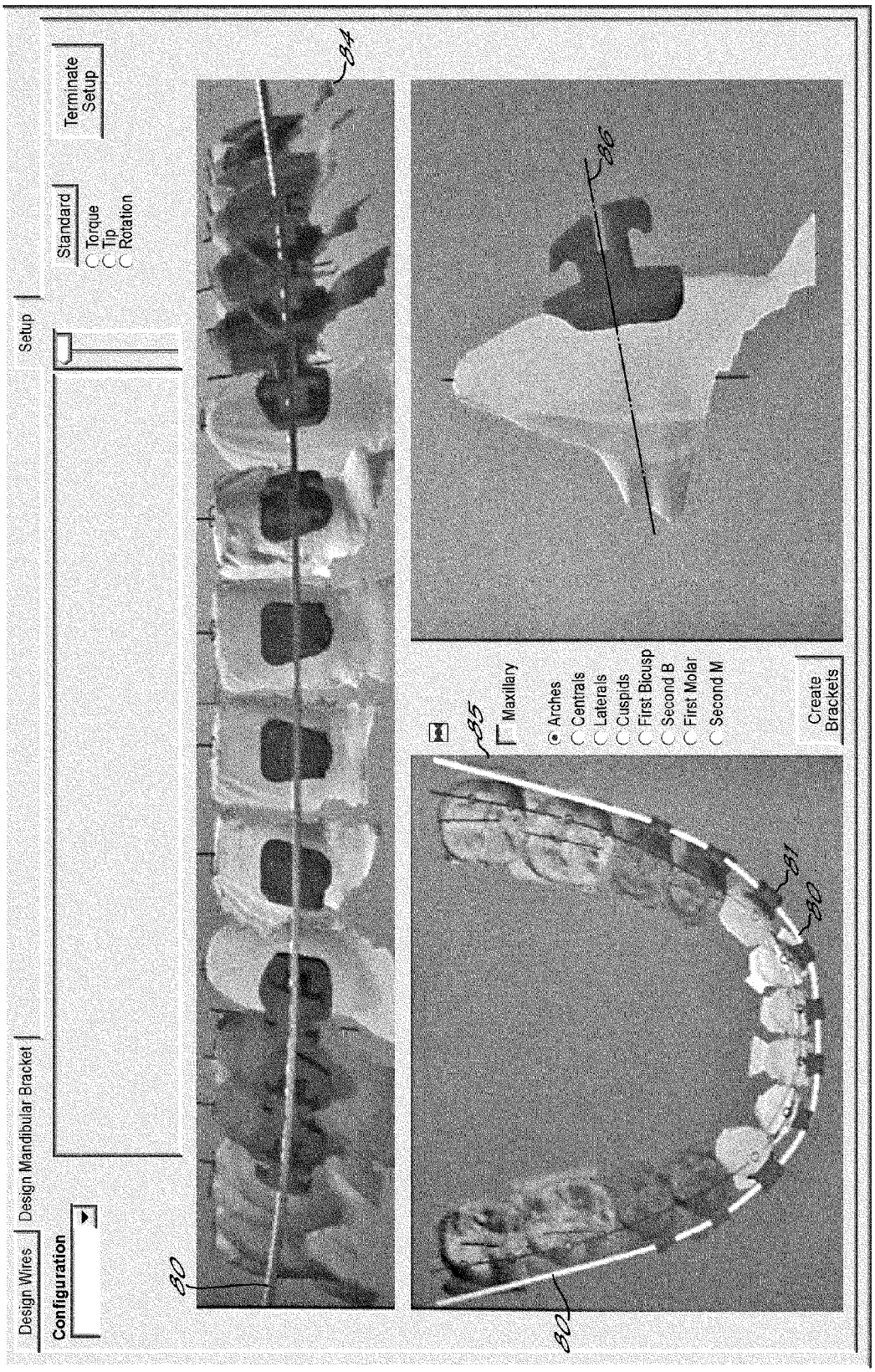
FIG. 5E is a display of the appliance facility, computer, similar to FIG. 5A, displaying various views of the patient's teeth, in high resolution, three-dimensional solid images, in relative posttreatment positions with a custom designed appliance thereon.
Figure 5F:
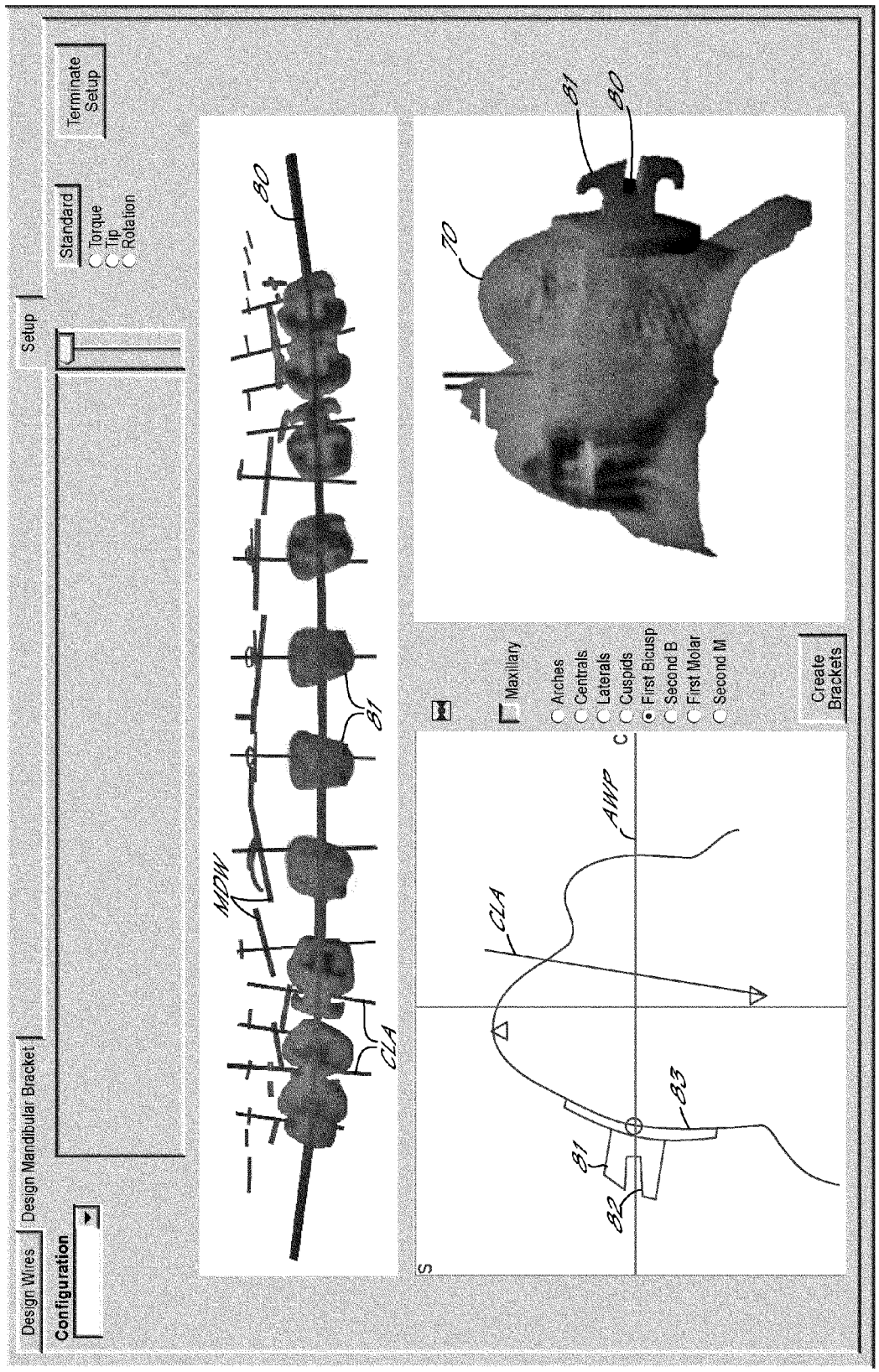
FIG. 5F is a display of the appliance facility computer with a selected screen window enlarged and illustrating a tooth cross section with a custom designed bracket of the appliance of FIG. 5E positioned thereon, and illustrating a hybrid perspective view of simplified vector images and solid three-dimensional images of the mandibular teeth of the patient in the posttreatment positions with the custom designed appliance thereon.

The feedback information can include information approving tooth positions and orientations toward which the teeth of the patient are to be moved by the appliance. For example, when the tooth finish positions have been finally calculated following the iterations between the computer 30b and the orthodontist, the orthodontist communicates satisfaction with the treatment positions to the appliance design facility 13 and the operator thereat then commands the computer 30b, or the computer can be respond automatically, to design the appliance. In designing an appliance according to conventional straight-wire orthodontic appliance techniques, the appliance will be one made up of brackets to be bonded to the patient's teeth which support an interconnecting archwire. The straight wire appliance design proceeds with the design of an archwire, the design of brackets and the design of bracket placement jigs, all custom to the treatment plan approved by the orthodontist for the specific patient. The design of archwires can be carried out in accordance with the patents incorporated above, such as U.S. Pat. Nos. 5,454,717 and 5,447,432. Archwire designing concepts such as those discussed in U.S. Pat. No. 5,474,448, hereby expressly incorporated by reference herein, are also particularly suitable. Archwire design places an archwire 80 at an optimal low profile position relative to each of the teeth, as illustrated in FIG. 5E for the mandibular arch. The archwire 80 is designed to lie in an archwire plane AWP through the teeth when the teeth are in their posttreatment or finish positions, as illustrated in FIG. 5F for a mandibular first bicuspid. Once the archwire 80 has been designed, brackets 81 are automatically designed by the computer 30b to form the connection between the archwire 80 and the patient's tooth, with the shape of the custom archwire 80 defining an archwire slot 82 in the bracket 81 and the three-dimensional data from the 3-D high resolution data file for the tooth defining the contour of the bracket mounting base 83. To facilitate the proper identification of the brackets to the teeth on which they belong, these bracket mounting bases are preferably shaped in accordance with the concepts described in U.S. Pat. No. 5,993,206, hereby expressly incorporated by reference herein, with the bases thereof being scaled reductions of the profiles of the crowns of the teeth viewed from the facial side.

Figure 5G:
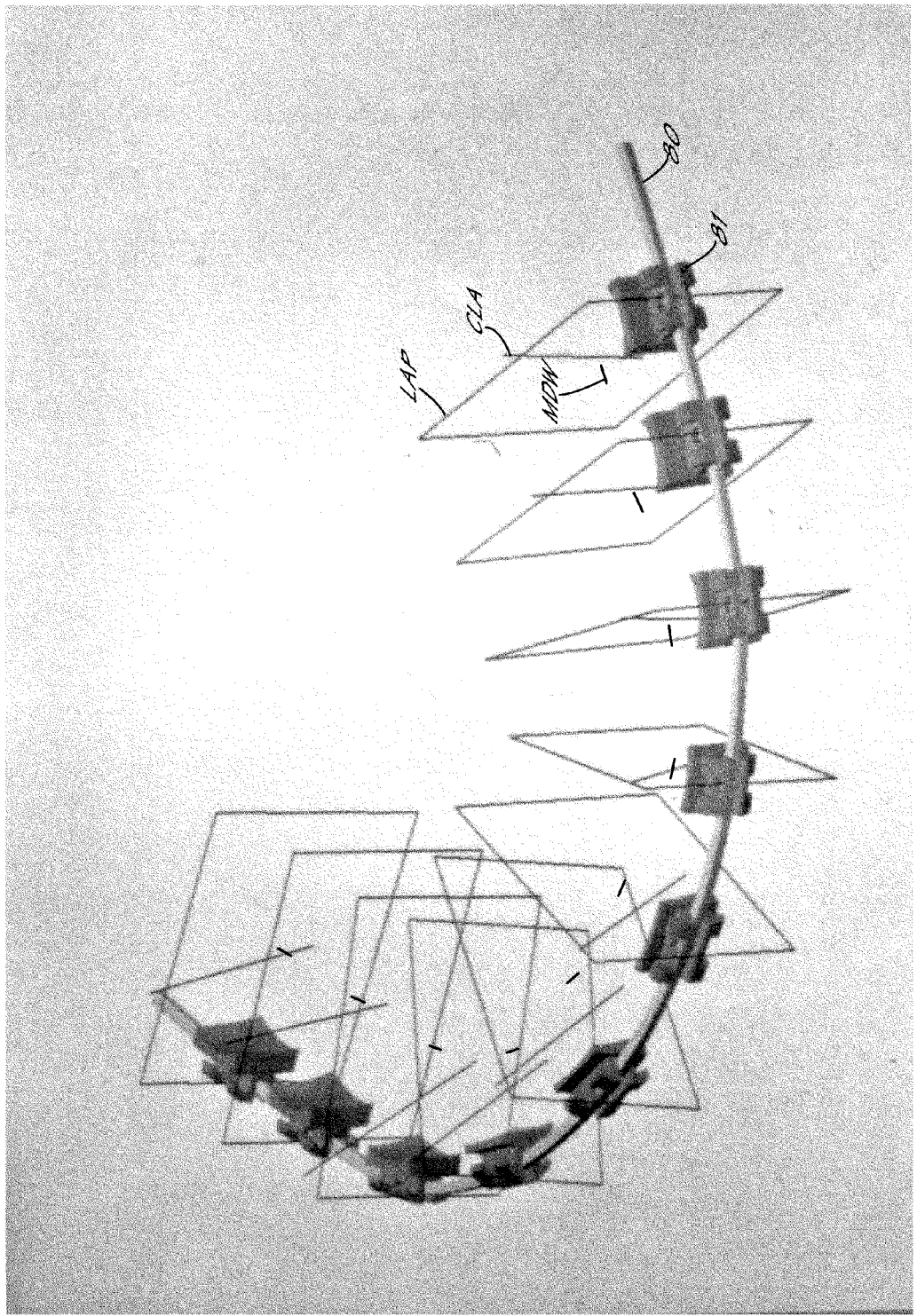
FIG. 5G is a display of the appliance facility computer illustrating a selected screen window showing an alternative hybrid perspective view to that of FIG. 5F of simplified vector images and solid three-dimensional images of the mandibular teeth of the patient in the posttreatment positions with the custom designed appliance thereon.

The screen of FIG. 5E illustrates an automatically designed appliance on three-dimensional solid images of the mandibular teeth, shown in a facial view screen window 84 and an occlusal view window 85. With this screen, a user can select the individual teeth to display in an individual tooth window 86, and can also display the cross-sectional view of the tooth as illustrated in FIG. 5F. The appliance formed of the archwire 80 and brackets 81 is illustrated on vector images of the teeth in a perspective view in FIG. 5G, which can also be selected by a user for display. As with the positioning of the teeth, the design of the appliance can be adjusted by a user, who may be either the operator 28 at the appliance design facility 13 or the orthodontist 14 on a computer at the office 11. In particular, the orthodontist can adjust the torque, tip and rotation of the brackets just as these parameters of the tooth were adjusted in arriving at the tooth finish positions, so as to change the relationship of the archwire slot relative to the tooth. The bracket location on the surface of the tooth can also be adjusted by the orthodontist. Similarly, the archwire can be reshaped. When these changes to the appliance have been made by the orthodontist, the appliance design may be recalculated. In addition, the tooth treatment or finish positions can be recalculated and the recalculated positions displayed to show the effects, if any, that changes to the appliance design would cause to the relocations of the teeth when treated with such an appliance.

Figure 6:
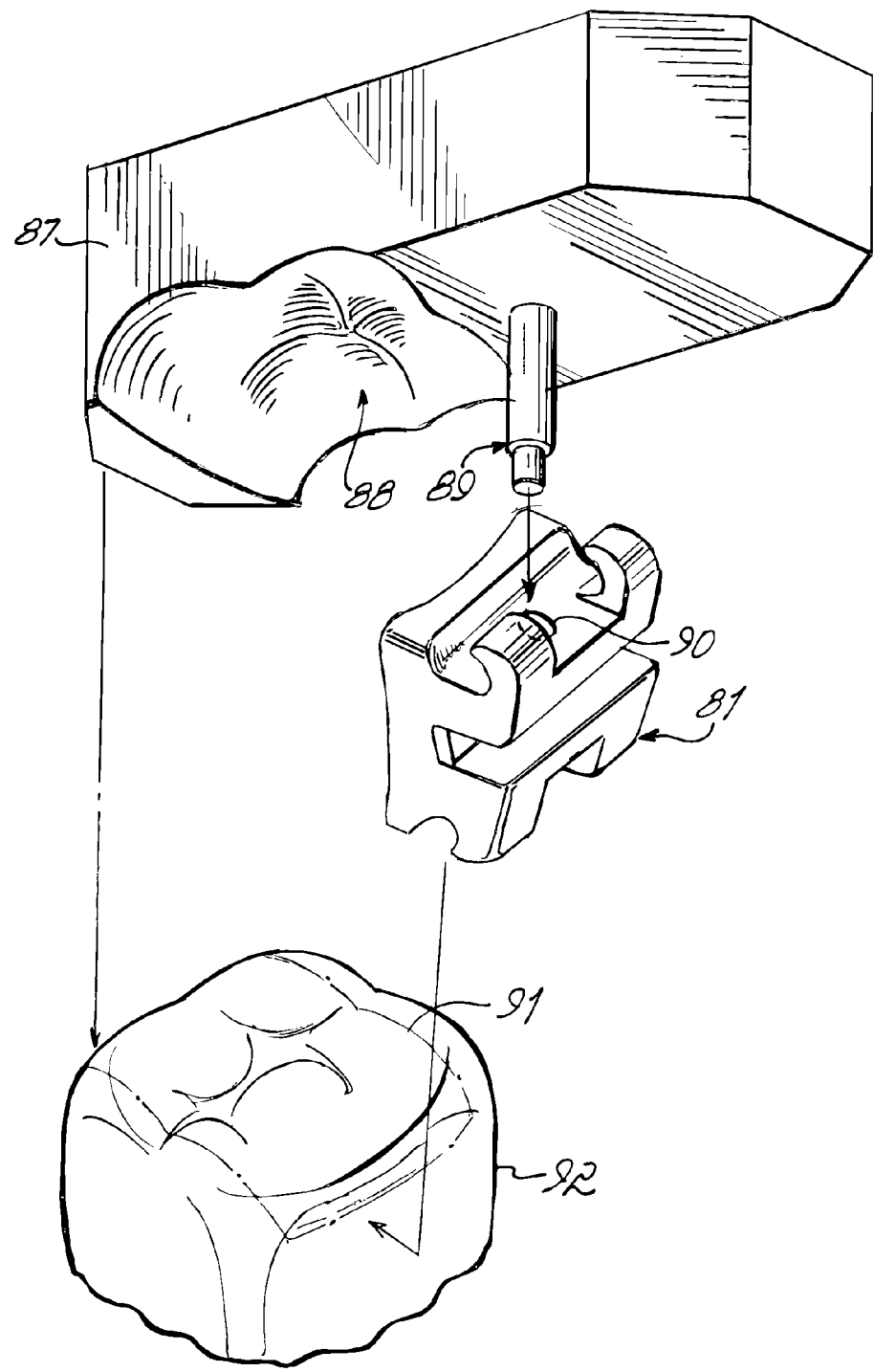
FIG. 6 is a disassembled perspective view of a custom designed bracket and the corresponding custom designed bracket placement jig therefore illustrated in relation to the tooth on which the bracket is to be placed.

Once the archwire 80 and brackets 81 have been designed and the positions of the brackets on the teeth determined, jigs 87 are automatically designed by the computer 30b. From bracket design and positioning information and from the high resolution, three-dimensional data of the shape of the teeth, the jigs 87 are designed so that they fit at a unique location, and orientation on the occlusal surface of the crown of one of the teeth 92 so that the corresponding custom bracket 81 for that tooth is precisely supported at its calculated placement position on the tooth 92 during the bonding of the bracket 81 to the tooth with adhesive by the orthodontist. FIG. 6 illustrates such a jig 87 as a solid three-dimensional object, dimensioned and positioned to intersect the one of the teeth 92 on which a bracket 81 is to be placed. The bracket is shaped and placed so as to avoid interference with adjacent teeth in either their pretreatment or posttreatment positions and during the movement of the tooth during treatment.

In particular, the body of the jig 87 is designed to have a cavity 88 on one side thereof to fit precisely against the occlusal surface 91 of one, and only one, of the patient's teeth 92. The surface of the cavity 88 has a shape defined by the high resolution, three-dimensional data of the occlusal surface 91 of the tooth over which the jig 87 is to fit. The jig 87 has a bracket engaging element 89 configured to removably connect to a bracket 81, which has a hole 90 in the archwire support 94 thereof to receive the element 89. The element 89 is in the form of a cylindrical post having a shoulder thereon to fix the spacing of the bracket from the jig. When assembled for shipment to the orthodontist, the element 89 is lightly bonded to the bracket with wax or adhesive. When the jig 87 is fit on the crown of the tooth, the bracket 81 is positioned and oriented in one, and only one, way on the tooth because the bracket 81, and particularly the archwire slot 82 thereof, is in a specific design position and orientation relative to the surface of the cavity 88 when the jig and bracket assembly are placed on the tooth. When the jig 87 is so positioned on the crown of a tooth with the cavity 88 conforming exactly to the occlusal surface of the tooth, the base 83 of the bracket 81 is supported in a predetermined position on the tooth according to the automated custom appliance design. When bonded with adhesive in this position on the tooth, the archwire slot 82 of the bracket 81 will be located at its design position and orientation relative to the occlusal surface 91 of the tooth 92.

The design of the custom orthodontic appliance produces data files 36 from which automatic manufacturing equipment can be controlled to produce archwires and brackets and the jigs for installation of the brackets at design locations on the patient's teeth, or other appliances. Most archwires, such as those made of stainless steel, can be made on wire bending machines controlled by signals that represent the wire as a curvature that is a function of the wire length from end to end. Such a wire bender is described, for example, in U.S. Pat. No. 5,447,432. Wires are sometimes desired that are highly elastic and formed of materials such as titanium alloys that cannot be easily or accurately formed by bending. Such wires can be formed on equipment such as the wire forming system of the type illustrated in FIG. 7.

Figure 7:
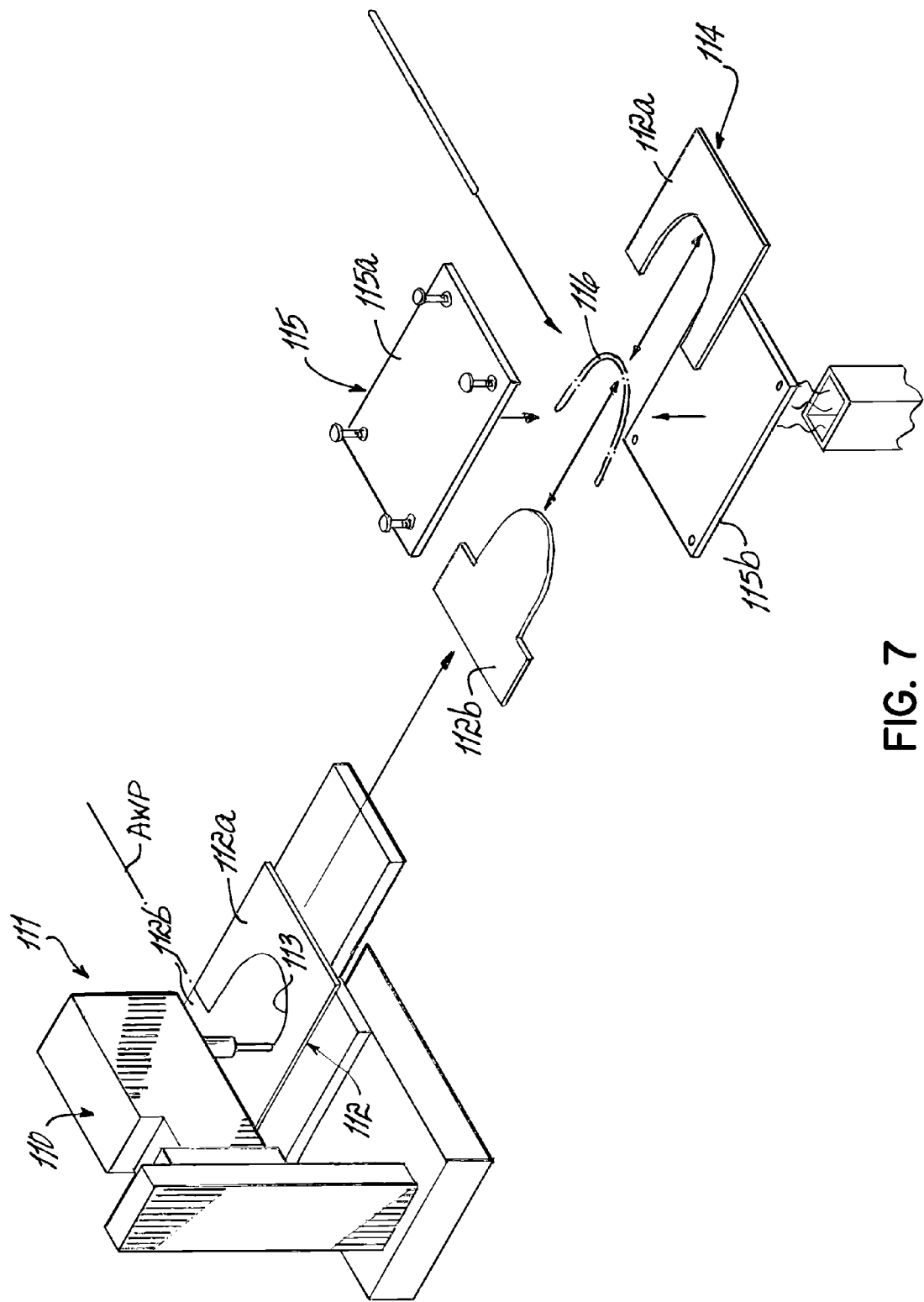
FIG. 7 is a sequential perspective diagram of a custom archwire forming system according to one embodiment of the system of FIG. 1.
Figure 8A:
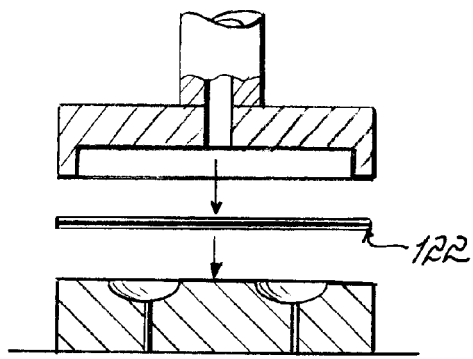
FIGS. 8A-8D are sequential diagrams of a custom bracket forming system according to one embodiment of the system of FIG. 1.
Figure 8B:
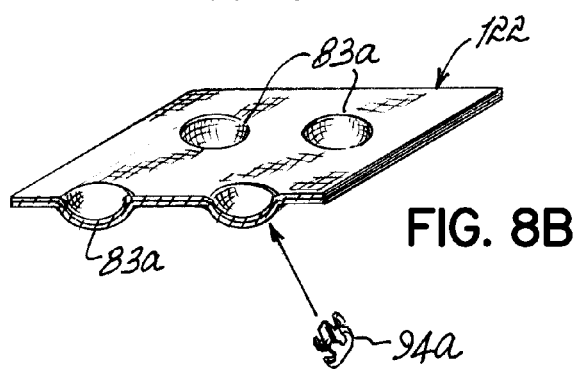
Figure 8C:
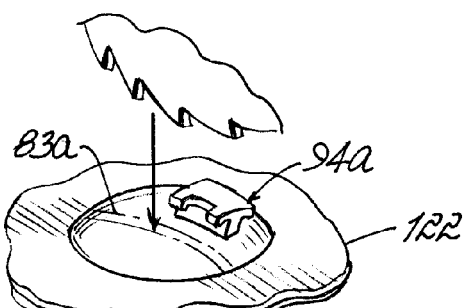
Figure 8D:
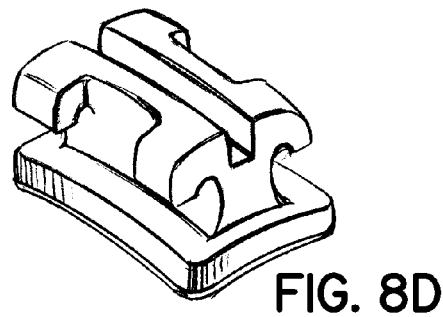

The system 110 of FIG. 7 uses a mill 111 to form a cut 113 that is the shape of an archwire as it appears in the archwire plane AWP through a sheet 112 of metal, ceramic, machinable rigid foam or other temperature resistant material that is about 0.01 inch thick. The cut 113 that is the shape of the archwire separates the sheet 112 into two parts, 112a, 112b, which are inserted into opposite ends of a slot 114 which is formed in a ceramic block 115. The block 115 is formed of two parts 115a, 115b that are pinned together to define the slot 114 between them. A blank length of archwire material 116 is inserted into the slot 114 between the halves 115a, 115b of the block 115. Then, the two parts 112a, 112b of the sheet 112 are inserted into the slot 114, and brought together on opposite sides of the wire 116, so as to clamp the wire blank 116 between the sheet halves 112a, 112b in a groove that is the shape of the cut 113 of the custom archwire 80, described above. The block 115 is then heated until the wire blank 116 is annealed and permanently assumes the shape of the cut 113. The block 115 and sheet halves 112a, 112b are then separated and the wire 116 that is formed in the shape of the custom archwire 80 is removed.

The automatic formation of custom brackets is accomplished by one of several systems, one being that described in U.S. Pat. No. 5,454,717, in which individual bracket blanks are mounted in separate fixtures on the workpiece holder of a mill and the slots are cut at custom locations and orientations in the archwire support of the bracket, which is then welded to a bonding base that is preformed to a standard curvature of a tooth. One alternative bracket manufacturing system that uses bases having standardized curvatures is the system 120 illustrated in FIGS. 8A-8D. The system 120 uses a die assembly 123 which has a plurality of recesses 121 therein, each having a curvature conforming to the standard or statistically average curvature of a respective one of a patient's teeth at the point on the facial side (or lingual side in the case of lingual appliances) of the crown at which an orthodontic bracket is typically attached. A single sheet 122 of deformable metal material of a type and thickness out of which bracket bonding bases 83a can be formed is placed into the die assembly 123, and the sheet 122 is deformed such that a portion of it conforms to each of a plurality of cavities or recesses 121, one cavity for each bracket of a set. The force to deform the sheet 122 may be applied directly against the sheet 122 by static fluid pressure, preferably, using a liquid such as an oil.

When the sheet 122 has been deformed, a layer of wire mesh 124 is welded to the side thereof that includes the usually concave sides of the bracket bonding bases 83a. On the opposite and usually convex side of each of the bases 83a is welded a blank archwire support 94a of an orthodontic bracket. Then, the sheet 122 with each of the archwire supports 94a welded thereto is mounted on a slot cutting mill 125, which cuts the slots in all of the archwire supports 83a of all of the brackets. Each of the bases are then cut from the sheet 122 using a laser cutter or some other cutter that is, preferably, computer controlled.

Figure 9A:
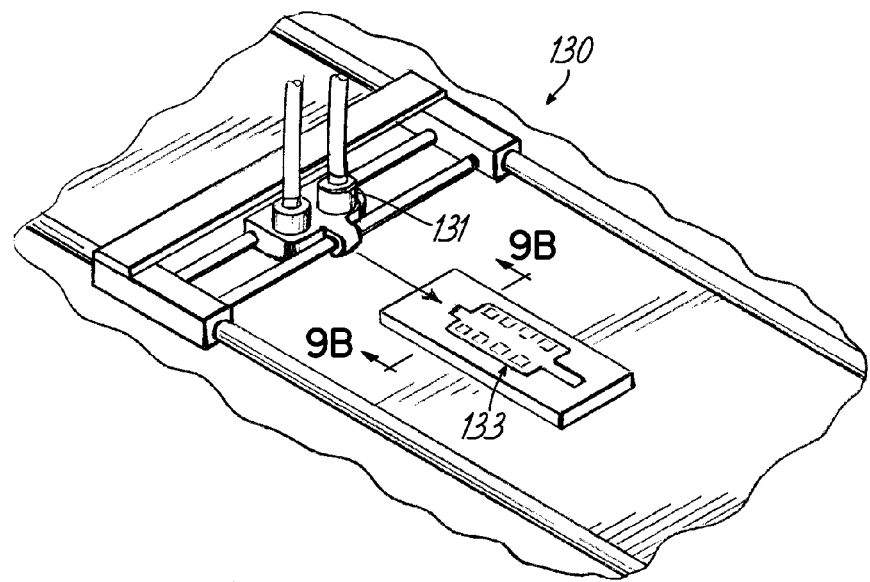
FIGS. 9A-9C are perspective diagrams of a custom bracket forming system according to another embodiment of the system of FIG. 1.
Figure 9B:
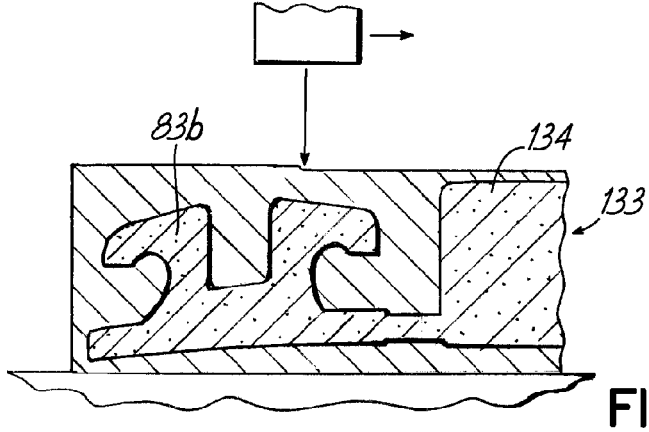
Figure 9C:
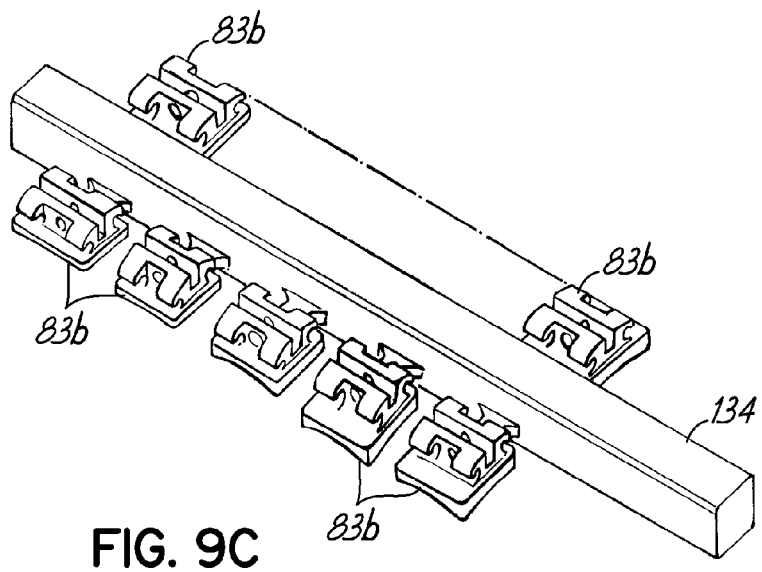

Another alternative system for automatically forming custom brackets is the system 130 illustrated in FIGS. 9A-9C. In the system 130, custom brackets 83b are formed in layers, for example, by jet printing of material to build up the bracket in layers by a stereo-lithography process. The printing of the material can be by directly depositing material of which the brackets are made to thereby form the bracket or to deposit wax or other pattern material to form a pattern from which a mold can be made to cast the bracket, such as by an investment casting method. In one such version of the system 130, a print head 131 is set up to jet print two types of wax, one which will either be melted or dissolved away, which is deposited on the portions of each layer that are external to the bracket being formed, and the other type of wax, which is deposited on portions interior to the bracket being formed, which will remain. An object 133 that is printed with such a method is either heated or chemically treated so as to remove the wax that is external to the bracket, leaving only the wax internal to the bracket, which is now a pattern in the shape of the bracket to be formed. The wax which becomes the pattern, may, for example, be of a higher melting point than the other wax or may be of a type that is insoluble in a solvent that will dissolve the other wax. The waxes are deposited in uniform layers, with the wax that is to form the pattern being deposited in the shape of a cross section or slice of the bracket and the other wax occupying the other areas of the layer that are to be removed. The layer is thereby deposited as a uniform thickness of the two waxes, with the pattern cross section defined by the one wax and the area around the pattern defined by the other. The wax around the pattern may, therefore, be selectively melted or dissolved away, leaving only a wax pattern in the shape of the appliance to be molded.

With such a system, the object may include a set of custom brackets 83*b* made according to the design method described above, interconnected by a stem 134, formed in a mold made from a pattern 135 formed out of the wax type that will remain after treatment, which can form the wax pattern for use in an otherwise conventional investment casting method of manufacture of the brackets. With such a method, the wax pattern made of the remaining wax is set in plaster or some other medium and the remaining wax is either burned out or evaporated. Then metal is injected into the mold cavity forming the custom brackets 83*b*. Brackets 83*b* made by this method can have not only custom located archwire slots but will have custom curved bases formed to precisely match the curvature of the teeth from the high resolution, three-dimensional data thereof. By printing in layers, the layers can be of the same approximate thickness as the resolution of the dots of wax being printed, thereby providing the same resolution in the direction perpendicular to the layers as exists in the planes of the layers.

Use of printing techniques to produce brackets, preferably layer by layer, is capable of producing brackets and other appliances or appliance components having full three-dimensional properties. This method is particularly useful for brackets made of materials such as plastic or ceramic that are not as easily machined, which can then be molded in molds made by this process. With such brackets, the bases can be shaped to conform precisely to the three-dimensional curvature of the surface of the tooth at the ideal placement position for the bracket on the tooth. Torque of the bracket can be built into the base of the bracket rather than being built into the archwire slot by controlling the angle of the slot.

Brackets can be made according to the system 130 by printing the material of which the bracket is to be made, such as metal, plastic or ceramic, rather than printing a material of which a pattern is made, such as wax. This direct stereo lithographic printing eliminates the need to cast a custom mold for the appliance around a pattern, then injecting the mold with appliance forming material to form the appliance. Methods of manufacture are known or are evolving by which materials, such as, for example, metal or ceramic, can be provided in powder form mixed with a binder. Such a material could then be deposited in a layer in the shape of the cross section of an appliance, with the area around the shape being formed only of a binder like material. The deposition may be by printing. Like the pattern printed for the investment casting method, the binder can be removed by heat or solvent, leaving a bracket or other appliance or appliance part formed of the material in the three-dimensional shape of the orthodontic appliance. Instead of making a mold of the material, after all layers have been applied to produce the three-dimensional appliance, the material, which is metal, ceramic or other material, and which is relatively fragile with the binder removed, is then heated to just below its melting point, and sintered until it achieves the desired cohesion and density. Such sintering usually results in shrinkage which must be accounted for by enlarging, the shape of the appliance cross sections being printed by a scale that compensates for the predicted shrinkage.

Other techniques for producing the appliance in layers may be used, with each layer being controlled by the manufacturing computer 30*c* to conform to the shape of the custom appliance design. Materials may, for example, be deposited in uniform layers, with a cross section of the appliance then being bonded, such as for example, being sintered with the use of a computer controlled laser, for example, in the shape of the custom appliance design. After all of the layers have been applied, the material which has not been so bonded is removed leaving a three-dimensional appliance. The laser, or other energy source, photographically exposes the material in a way similar to that used in patterning photo-resist film in the manufacture of semiconductors, thereby fixing the material so that it can be selectively removed to produce a bracket shaped object.

Figure 6A:
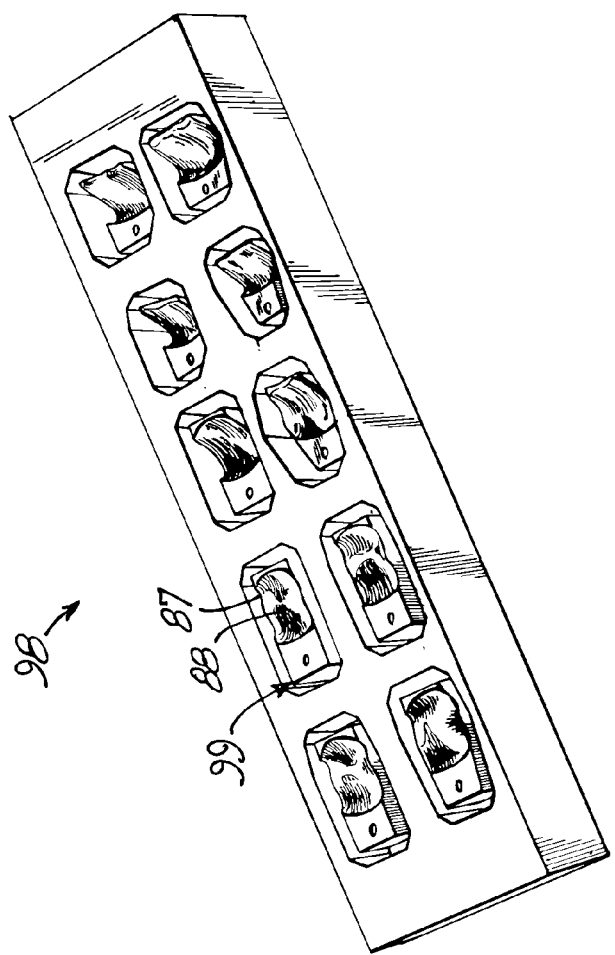
FIG. 6A is a perspective view of a set of custom jigs formed according to one embodiment of the system of FIG. 1.
Figure 6B:
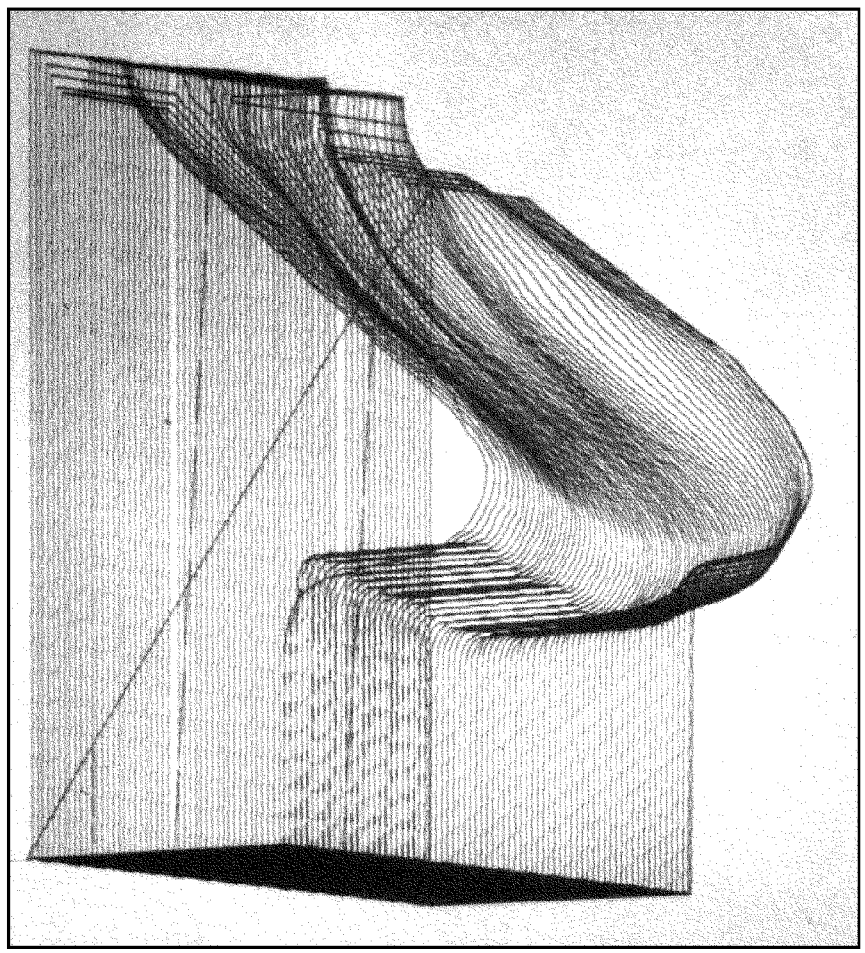
FIG. 6B is a perspective diagram illustrating the milling of a custom jig of FIG. 6A.

Brackets may be configured with surfaces on them that facilitate their positioning on a patient's teeth using separate jigs or a separate surface on the bracket in lieu of jigs. In the bracket illustrated in FIG. 6, for example, the vertical hole 90 is formed in the archwire support for the removable connection thereto of a post-like element 89 of a jig 87. The manufacture of the jigs for positioning such brackets may be carried out with any of several manufacturing techniques that will reproduce the precise shape of the tooth crown occlusal surface 91 in the jig 83, so that the jig will fit in one, and only one, position and orientation on the crown of the tooth of the patient to which a custom appliance is to be bonded. A suitable method to make such a jig, is to machine the cavity 88 of the jig 87 out of a rigid foam material using a precision computer controlled mill sized and configured for that purpose. One such material is LAST-A-FOAM type FR3720 manufactured by General Plastics Mfg. Co. of Tacoma Wash. Preferably, a set of all of the jigs required to neat a particular patient is formed of a single integral block 98 of the foam material, as illustrated in FIG. 6A. The block thereby facilitates the holding of the jigs for machining. A channel 99 may be cut by the mill around each jig so that by simply slicing the upper surface of the foam from the block of foam, the individual jigs may be separated. The crown surface cavities 88 are cut into the jigs 87 in accordance with the three-dimensional data from the high resolution 3-D data file, as illustrated in FIG. 6B. The portion of the data used to define the shape is determined in the appliance design process wherein the bracket placement positions on the patient's teeth are calculated.

What is described above includes the preferred embodiments of the invention. Those skilled in the art will appreciate that additions to and modifications of the system and method of the invention, and the detailed manifestations thereof, may be made without departing from the principles of the inventive concepts set forth herein.

Accordingly, the following is claimed:

1. A method of providing a custom orthodontic appliance for repositioning teeth of a patient, the method comprising:
   receiving a prescription for treatment of the patient from an orthodontic physician;
   providing for display on a computer screen, with interaction by an operator other than the physician, data of images of the teeth of the patient in suggested post-treatment tooth positions and orientations that are based on three-dimensional information of the shapes of the teeth of the patient;

receiving feedback information on the suggested post-treatment positions and orientations from the orthodontic physician who prescribed treatment of the patient, after the physician has interactively viewed a display of the provided images on the computer screen; and providing a custom orthodontic appliance configured to reposition teeth of the patient based on the suggested tooth positions and orientations in accordance with the feedback information from the orthodontic physician.

2. The method of claim 1 wherein:

the feedback information includes information of approval by the orthodontic physician of the suggested post-treatment tooth positions and orientations toward which the teeth of the patient are to be moved by the appliance.

3. The method of claim 1 wherein:

the feedback information includes information of a change in position or orientation of at least one tooth from the suggested post-treatment tooth positions and orientations toward which the at least one tooth of the patient is to be moved by the appliance.

4. The method of claim 3 further comprising:

providing revised images of the teeth of the patient for redisplay in revised post-treatment tooth positions and orientations based on the suggested tooth positions and orientations as changed in accordance with the feedback information.

5. A method of providing a custom orthodontic appliance configured to the individual anatomy of a patient for repositioning teeth of the patient, the method comprising:

receiving a prescription for treatment of the patient from an orthodontic physician;

providing for display on a computer screen images of the teeth of the patient in suggested post-treatment tooth positions and orientations that are based on three-dimensional information of the shapes of the teeth of the patient;

receiving feedback information on the suggested post-treatment positions and orientations from the orthodontic physician who prescribed treatment of the patient, after the physician has interactively viewed a display of the provided images on a computer screen;

wherein the feedback information includes one or more of:
information approving at least some of the suggested post-treatment positions and orientations, and
information changing at least one of the suggested post-treatment tooth positions or orientations; and providing a custom orthodontic appliance configured to reposition teeth of the patient based on the suggested post-treatment tooth positions and orientations in accordance with the feedback information.

6. The method of claim 5 further comprising:

providing revised images of the teeth of the patient in revised post-treatment tooth positions and orientations based on the suggested post-treatment tooth positions and orientations as changed in accordance with the feedback information.

7. The method of claim 6 further comprising:

receiving from the orthodontic physician who has viewed a display of the provided revised images feedback information approving the revised post-treatment tooth positions and orientations toward which the teeth of the patient are to be moved by the appliance.

8. The method of claim 5 further comprising:

providing the orthodontic physician viewing the display with a capability to enter the feedback information.

9. The method of claim 5 wherein: the interactive viewing comprises the orthodontic physician graphically repositioning at least one tooth.

10. A method of providing a custom orthodontic appliance, configured to the individual anatomy of a patient, for orthodontically repositioning teeth of the patient, the method comprising:

receiving a prescription for treatment of the patient from an orthodontic physician;

providing digital data of suggested post-treatment tooth positions and orientations of teeth of the patient that are based on three-dimensional information of the shapes of the teeth of the patient;

providing images of teeth of the patient from the digital data, for display on at least one computer screen to the orthodontic physician who prescribed treatment of the patient in the suggested post treatment tooth positions and orientations for either (a approval for use in creating a custom orthodontic appliance for the patient or (b revision;

receiving from the orthodontic physician, after the physician has interactively viewed on a computer screen a display of the provided images, feedback information approving the suggested post-treatment positions and orientations; and providing a custom orthodontic appliance configured to the individual anatomy of the patient to reposition teeth of the patient based on the suggested post-treatment tooth positions and orientations approved in accordance with the feedback information.

11. The method of claim 10 wherein the receiving of the feedback information approving the suggested post-treatment positions and orientations for a custom orthodontic appliance for the patient includes:

receiving from the orthodontic physician, after the physician has interactively viewed on a computer screen a display of the provided images, feedback information of revisions to the suggested post-treatment positions and orientations;

providing further images of teeth of the patient based on the three dimensional information, for redisplay on the computer display device to the orthodontic physician, in suggested post-treatment tooth positions and orientations that have been changed in accordance with the feedback information of the revisions; and receiving from the orthodontic physician, after the physician has viewed a redisplay of the provided further images on a computer screen, the feedback information approving the suggested post-treatment positions and orientations, as changed in accordance with the feedback information of the revisions.

12. The method of claim 11 wherein: the providing of digital data of suggested post-treatment tooth positions and orientations of teeth of the patient that are based on three-dimensional information of the shapes of the teeth of the patient includes providing for display on a computer screen, with interaction by an operator, the digital data; and the orthodontic physician who has interactively viewed on a computer screen a display of the provided images is a person other than the operator.

13. The method of claim 11 wherein:

the receiving of feedback information from the orthodontic physician approving the suggested post-treatment positions and orientations includes receiving feedback information wherein the feedback information can include either information approving the suggested post-treatment tooth positions and orientations or information modifying at least one of the suggested post-treatment tooth positions or orientations.

* * * * *